(12) United States Patent
Loughney

(10) Patent No.: US 6,350,603 B1
(45) Date of Patent: Feb. 26, 2002

(54) PHOSPHODIESTERASE 10

(75) Inventor: Kate Loughney, Seattle, WA (US)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 09/256,000

(22) Filed: Feb. 23, 1999

Related U.S. Application Data

(60) Provisional application No. 60/075,508, filed on Feb. 23, 1998.

(51) Int. Cl.$^7$ ............................. C12N 9/16; C12N 1/20; C12N 15/63; C07H 21/04
(52) U.S. Cl. .................. 435/196; 435/69.1; 435/252.3; 435/320.1; 435/325; 530/350; 536/23.1; 536/23.2
(58) Field of Search ................................ 435/196, 69.1, 435/252.3, 320.1, 325; 530/350; 536/23.1, 23.2

(56) References Cited

U.S. PATENT DOCUMENTS

| | | | |
|---|---|---|---|
| 5,389,527 A | 2/1995 | Beavo et al. | 435/69.1 |
| 5,922,595 A | 7/1999 | Fisher et al. | 435/320.1 |

FOREIGN PATENT DOCUMENTS

| | | |
|---|---|---|
| WO | WO 91/09955 | 7/1991 |
| WO | WO 92/20808 | 11/1992 |
| WO | WO 94/12650 | 6/1994 |
| WO | WO 97/09433 | 3/1997 |

OTHER PUBLICATIONS

NCI–CGAP, National Cancer Institute, Cancer Genome Anatomy Project (CGAP), Genbank Accession No:AA502909, Aug. 19, 1997.*
Hillier et al. The WashU–Merck EST Project, Genbank Accession No: R19767, Apr. 17, 1995.*
Fisher, et al., "Isolation and Characterization of PDE9A, a Novel Human cGMP–specific Phosphodiesterase*," *Journal of Biological Chemistry* 273:15559–15564 (1998).
Mukai, et al., "Separation and characterization of a novel isoenzyme of cyclic nucleotide phosphodiesterase from rat cerebrum," *Br. J. Pharmacol.* 111:389–390 (1994).
Soderling, et al., "Identification and Characterization of a Novel Family of Cyclin Nucleotide Phosphodiesterases*," *Journal of Biological Chemistry* 273:15553–15558 (1998).
Anderson, "Human gene therapy," *Nature*, supplement to vol. 392, No. 6679, p. 25 (1998).
Ausebel, et al., "Screening of Recombinant DNA Libraries," *Current Protocols in Molecular Biology*, John Wiley & Sons, pp. 6.0.3–6.4.10 (1994).
Avramopoulos, et al., "Linkage mapping of the cystathionine β–synthase (CBS) gene on human chromosome 21 using a DNA polymorphism in the 3' untranslated region," *Hum. Genet.* 90:566–568 (1993).

Beavo, "Cyclic Nucleotide Phosphodiesterases: Functional Implications of Multiple Isoforms," *Physiol. Rev.* 75:725–748 (1995).
Bolger, et al., "A Family of Human Phosphodiesterases Homologous to the dunce Learning and Memory Gene Product of *Drosophila melanogaster* Are Potential Targets for Antidepressant Drugs," *Mol. Cell. Biol.* 13:6558–6571 (1993).
Bolger, et al., "Characterization of five different proteins produced by alternatively spliced mRNAs from the human cAMP–specific phosphodiesterase PDED gene," *Biochem. J.* 328:539–548 (1997).
Bonne–Tamir, et al., "Linkage of Congenital Recessive Deafness (Gene DFNB10) to Chromosome 21q22.3," *Am. J. Hum. Genet.* 58:1254–1259 (1996).
Boolell, et al., "Sildenafil: an orally active type 5 cyclic GMP–specific phosphodiesterase inhibitor for the treatment of penile erectile dysfunction," *Int. J. Impotence Res.* 8:47–50 (1996).
Bramlage, et al., "Designing ribozymes for the inhibition of gene expression," *Trends in Biotech* 16:434–438 (1998).
Cane, et al., "Harnessing the Biosynthetic Code: Combinations, Permutations, and Mutations," *Science* 282:63–68 (1998).
Capecchi, "Altering the Genome by Homologous Recombination," *Science* 244:1288–1292 (1989).
Charbonneau, et al., "Identification of a conserved domain among cyclic nucleotide phosphodiesterases from diverse species," *Proc. Natl. Acad. Sci. (USA)* 83:9308–9312 (1986).
Collins, et al., "The Human β–Subunit of Rod Photoreceptor cGMP Phosphodiesterase: Complete Retinal cDNA Sequence and Evidence for Expression in Brain," *Genomics* 13:698–704 (1992).
Coste, et al., "Characterization of a Novel Potent and Specific Inhibitor of Type V Phosphodiesterase," *Biochem. Pharmacol.* 50:1577–1585 (1995).
Delabar, et al., "Molecular Mapping of Twenty–Four Features of Down Syndrome on Chromosome 21," *Eur. J. Hum. Genet.* 1:114–124 (1993).

(List continued on next page.)

*Primary Examiner*—Rebecca E. Prouty
*Assistant Examiner*—Richard Hutson
(74) *Attorney, Agent, or Firm*—Marshall, Gerstein, & Borun

(57) ABSTRACT

The present invention provides novel human PDE10 polypeptides, polynucleotides encoding the polypeptides, expression constructs comprising the polynucleotides, host cells transformed with the expression constructs; methods for producing PDE10 polypeptides; antisense polynucleotides; and antibodies specifically immunoreactive with the PDE10 polypeptides. The invention further provides methods to identify binding partners of PDE10, and more particularly, binding partners that modulate PDE10 enzyme activity.

12 Claims, No Drawings

OTHER PUBLICATIONS

Francis, et al., "Zinc Interactions and Conserved Motifs of the cGMP-binding cGMP-specific Phosphodiesterase Suggest That It is a Zinc Hydrolase*," *J. Biol. Chem.* 269:22477–22480 (1994).

Friedmann, "Progress Toward Human Gene Therapy," *Science* 244:1275–1281 (1989).

Gibson, et al., "Ribozymes: Their Functions and Strategies for Their Use," *Mol. Biotech.* 7:125–137 (1997).

Harbinson, et al., "The effect of a novel orally active selective PDE4 isoenzyme inhibitor (CDP840) on allergen–induced responses in asthmatic subjects," *Eur. Respir. J.* 10:1008–1014 (1997).

Harlow, et al., "Monoclonal Antibodies," *Antibodies: A Laboratory Manual*, Cold Spring Harbor Laboratory; Cold Spring Harbor, NY Chapter 6 (1988).

Harlow, et al., "Fusion by Stirring (50% PEG)*," *Antibodies, a Laboratory Manual*, Cold Spring Harbor Laboratory, p. 211 (1988).

Houston, et al., "The chemical–biological interface: developments in automated and miniaturised screening technology," *Curr. Opin. Biotechnol* 8:734–740 (1997).

Jayawickreme, et al., "Gene expression systems in the development of high–throughput screens," *Curr. Opin. Biotechnol.* 8:629–634 (1997).

Korenberg, et al., "Down syndrome phenotypes: The consequences of chromosomal imbalance," *Proc. Natl. Acad. Sci. (USA)* 91:4997–5001 (1994).

Lavrovsky, et al., "Therapeutic Potential and Mechanism of Action of Oligonucleotides and Ribozymes," *Biochem. Mol. Med.* 62:11–22 (1997).

Lehninger, "The Amino Acid Building Blocks of Proteins," *Biochemistry*, Second Edition; Worth Publishers, Inc. NY:NY pp. 71–77 (1975).

Loughney et al., "Isolation and Characterization of cDNAs Corresponding to Two Human Calcium, Calmodulin–regulated, 3',5'–Cyclic Nucleotide Phosphodiesterases*," *J. Biol Chem.* 271:796–806 (1996).

Loughney, et al., "Identification and Quantification of PDE Isoenzymes and Subtypes by Molecular Biological Methods," *Phosphodiesterase Inhibitors*, Academic Press: New York, New York pp. 1–19 (1996).

Manganiello, et al., "Cyclic GMP–Inhibited Cyclic Nucleotide Phosphodiesterases," *Isoenzymes of Cyclic Nucleotide Phosphodiesterases*, John Wiley and Sons, Ltd., pp. 87–116 (1990).

Manganiello, et al., "Perspectives in Biochemistry and Biophysics Isoenzyme Families," *Arch. Biochem. Acta* 322:1–13 (1995).

Meacci, et al., "Molecular cloning and expression of human myocardial cGMP–inhibited cAMP phosphodiesterase," *Proc. Natl. Acad. Sci. (USA)* 89:3721–3725 (1992).

Michaeli, et al., "Isolation and Characterization of a Previously Undetected Human cAMP Phosphodiesterase by Complementation of cAMP Phosphodiesterase–deficient *Saccharomyces cerevisiae*\*," *J. Biol. Chem.* 17:12925–12932 (1993).

Miki, et al., "Characterization of the cDNA and Gene Encoding Human PDE3B, the cGIP1 Isoform of the Human Cyclic GMP–Inhibited Cyclic Nucleotide Phosphodiesterase Family," *Genomics* 36:476–485 (1996).

Miller, "Human gene therapy comes of age," *Nature* 357:455–460 (1992).

Munke, et al., "The Gene for Cystathionine β–Synthase (CBS) Maps to the Subtelomeric Region on Human Chromosome 21q and to Proximal Mouse Chromosome 17," *Hum. Genet.* 42:550–559 (1988).

Myers, "Will combinational chemistry deliver real medicines?" *Curr. Opion. Biotechnol.* 8:701–707 (1997).

Pittler, et al., "Molecular Characterization of Human and Bovine Rod Photoreceptor cGMP Phosphodiesterase α–Subunit and Chromosomal Localization of the Human Gene," *Genomics* 6:272–283 (1990).

Piriev, et al., "Gene Structure and Amino Acid Sequence of the Human Cone Photoreceptor cGMP–Phosphodiesterase α' Subunit (PDEA2) and Its Chromosomal Localization to 10q24," *Genomics* 28:429–435 (1995).

Podzuweit, et al., "Isozyme Selective Inhibition of cGMP-–Stimulated Cyclic Nucleotide Phosphodiesterases by Erythro–9–(2–Hydroxy–3–Nonyl) Adenine," *Cell. Signaling* 7:733–738 (1995).

Price, et al., "Expression of Heterologous Proteins in *Saccharomyces cerevisiae* Using the *ADH2 Promoter*," *Meth. Enzymol.* 185:308–315 (1990).

Rosman, et al., "Isolation and characterization of human cDNAs encoding a cGMP–stimulated 3',5' –cyclic nucleotide phosphodiesterase[1]," *Gene* 191:89–95 (1997).

Sambrook, et al., "Hybridization of Radiolabeled Probes to Immobilized Nucleic Acids," *Molecular Cloning: A Laboratory Manual*, Cold Spring Harbor Laboratory Press: Cold Spring Harbor, New York (1989), pp. 9.47–9.51.

Tenor, et al., "Analysis of PDE4 Isoenzyme Profiles in Cells and Tissues by Pharmacological Methods," *Phosphodiesterase Inhibitors*, Academic Press: New York, New York pp. 21–40 (1996).

Sertie, et al., "A gene which causes severe ocular alterations and occipital encephalocele (Knobloch syndrome) is mapped to 21q22.3," *Hum. Mol. Genet.* 5:843–847 (1996).

Verma, "Treatment of disease by introducing healthy genes into the body is becoming feasible. But the therapy will not reach its full potential until the genes can be coaxed to work throughout life," *Scientific American* 68–84 (1990).

Vallada, et al., "Linkage studies in bipolar affective disorder with markers on chromosome 21," *J. Affect. Disord.* 41:217–221 (1996).

Veske, et al., "Autosomal recessive non–syndromic deafness locus (DFNB8) maps on chromosome 21q22 in a large consanguineous kindred from Pakistan," *Hum. Mol. Genet.* 5:165–168 (1996).

Yu, et al., "Identification and Characterisation of a Human Calmodulin–Stimulated Phosphodiesterase PDE1B1," *Cell Signaling* 9:519–529 (1997).

* cited by examiner

PHOSPHODIESTERASE 10

This application claims priority of U.S. Provisional Application No. 60/075,508, filed Feb. 23, 1998.

FIELD OF THE INVENTION

The present invention relates generally to a novel phosphodiesterase (PDE) designated PDE10. Depending on nomenclature used, PDE10 is also referred to as PDE9.

BACKGROUND OF THE INVENTION

Phosphodiesterases (PDEs) hydrolyze 3', 5' cyclic nucleotides to their respective nucleoside 5' monophosphates. The cyclic nucleotides cAMP and cGMP are synthesized by adenylyl and guanylyl cyclases, respectively, and serve as second messengers in a number of cellular signaling pathways. The duration and strength of the second messenger signal is a function of the rate of synthesis and the rate of hydrolysis of the cyclic nucleotide.

Multiple families of PDEs have been identified. The nomenclature system includes first a number that indicates the PDE family. To date, nine families (PDE 1–9) are known which are classified by: (i) primary structure; (ii) substrate preference; (iii) response to different modulators; (iv) sensitivity to specific inhibitors; and (v) modes of regulation [Loughney and Ferguson, in *Phosphodiesterase Inhibitors*, Schudt, et al. (Eds.), Academic Press: New York, N.Y. (1996) pp. 1–19]. The number indicating the family is followed by a capital letter, indicating a distinct gene, and the capital letter followed by a second number, indicating a specific splice variant or a specific transcript that utilizes a unique transcription initiation site.

The amino acid sequences of all mammalian PDEs identified to date include a highly conserved region of approximately 270 amino acids located in the carboxy terminal half of the protein [Charbonneau, et al., *Proc. Natl. Acad. Sci. (USA)* 83:9308–9312 (1986)]. The conserved domain includes the catalytic site for cAMP and/or cGMP hydrolysis and two putative zinc binding sites as well as family specific determinants [Beavo, *Physiol. Rev.* 75:725–748 (1995); Francis, et al., *J. Biol. Chem.* 269:22477–22480 (1994)]. The amino terminal regions of the various PDEs are highly variable and include other family specific determinants such as: (i) calmodulin binding sites (PDE1); (ii) non-catalytic cyclic GMP binding sites (PDE2, PDE5, PDE6); (iii) membrane targeting sites (PDE4); (iv) hydrophobic membrane association sites (PDE3); and (v) phosphorylation sites for either the calmodulin-dependent kinase II (PDE1), the cAMP-dependent kinase (PDE1, PDE3, PDE4), or the cGMP dependent kinase (PDE5) [Beavo, *Physiol. Rev.* 75:725–748 (1995); Manganiello, et al., *Arch. Biochem. Acta* 322:1–13 (1995); Conti, et al., *Physiol. Rev.* 75:723–748 (1995)].

Members of the PDE1 family are activated by calcium-calmodulin. Three genes have been identified; PDE1A and PDE1B preferentially hydrolyze cGMP while PDE1C has been shown to exhibit a high affinity for both cAMP and cGMP. The PDE2 family is characterized as being specifically stimulated by cGMP [Loughney and Ferguson, supra]. Only one gene has been identified, PDE2A, the enzyme product of which is specifically inhibited by erythro-9-(2-hydroxy-3-nonyl)adenine (EHNA). Enzymes in the PDE3 family are specifically inhibited by cGMP. Two genes are known, PDE3A and PDE3B, both having high affinity for both cAMP and cGMP, although the $V_{max}$ for cGMP hydrolysis is low enough that cGMP functions as a competitive inhibitor for cAMP hydrolysis. PDE3 enzymes are specifically inhibited by milrinone and enoximone [Loughney and Ferguson, supra]. The PDE4 family effects cAMP hydrolysis and includes four genes, PDE4A, PDE4B, PDE4C, and PDE4D, each having multiple splice variants. Members of this family are specifically inhibited by the anti-depressant drug rolipram. Members of PDE5 family bind cGMP at non-catalytic sites and preferentially hydrolyze cGMP. Only one gene, PDE5A, has been identified. The photoreceptor PDE6 enzymes specifically hydrolyze cGMP [Loughney and Ferguson, supra]. Genes include PDE6A and PDE6B (the protein products of which dimerize and bind two copies of a smaller γ inhibitory subunit to form rod PDE), in addition to PDE6C which associates with three smaller proteins to form cone PDE. The PDE7 family effects cAMP hydrolysis but, in contrast to the PDE4 family, is not inhibited by rolipram [Loughney and Ferguson, supra]. Only one gene, PDE7A, has been identified. The PDE8 family has been shown to hydrolyze both cAMP and cGMP and is insensitive to inhibitors specific for PDEs 1–5. Depending on nomenclature used, PDE8 is also referred to as PDE10, but is distinct from PDE10 described herein. The PDE9 family preferentially hydrolyzes cAMP and is not sensitive to inhibition by rolipram, a PDE4-specific inhibitor, or isobutyl methyl xanthine (IBMX), a non-specific PDE inhibitor. Depending on nomenclature used, PDE9 is also referred to as PDE8, but is distinct from PDE8 mentioned above. To date, two genes have been identified in the PDE9 family.

Specific and non-specific inhibitors of the various PDE protein families have been shown to be effective in treating disorders attributable, in part, to aberrant levels of cAMP or cGMP. For example, the PDE4-specific inhibitor rolipram, mentioned above as an anti-depressant, inhibits lipopolysaccharide-induced expression of TNFα and has been effective in treating multiple sclerosis in an animal model. Other PDE4-specific inhibitors are being investigated for use as anti-inflammatory therapeutics, and efficacy in attenuating the late asthmatic response to allergen challenge has been demonstrated [Harbinson, et al., *Eur. Respir. J.* 10:1008–1014 (1997)]. Inhibitors specific for the PDE3 family have been approved for treatment of congestive heart failure. PDE5 inhibitors are currently being evaluated for treatment of penile erectile dysfunction [Boolell, et al., *Int. J. Impotence Res.* 8:47–50 (1996)]. Non-specific inhibitors, such as theophylline and pentoxifylline, are currently used in the treatment of respiratory and vascular disorders, respectively.

Given the importance of cAMP and cGMP in intracellular second messenger signaling, there thus exists an ongoing need in the art to identify additional PDE species. Identification of heretofore unknown families of PDEs, and genes and splice variants thereof, will provide additional pharmacological approaches to treating conditions in which cyclic nucleotide pathways are aberrant, as well as conditions in which modulation of intracellular cAMP and/or cGMP levels in certain cell types is desirable. Identification of family-specific and enzyme-specific inhibitors will permit development of therapeutic and prophylactic agents which act on desired cell types expressing PDEs and/or particular metabolic pathways regulated by cyclic nucleotide monophosphate steady-state concentrations.

SUMMARY OF THE INVENTION

In brief, the prevent invention provides purified and isolated PDE10 polypeptides. Preferred polypeptides comprise the amino acid sequence selected from the group consisting of SEQ ID NO: 2, SEQ ID NO: 19, SEQ ID NO: 21 and SEQ ID NO: 23.

The invention also provides polynucleotides encoding polypeptides of the invention. A preferred polynucleotide comprises the sequence set forth in SEQ ID NO: 1. Polynucleotides of the invention include polynucleotides encoding a human PDE10 polypeptide selected from the group consisting of: a) the polynucleotide according to SEQ ID NO: 1, 18, 20 or 22; b) a DNA which hybridizes under moderately stringent conditions to the non-coding strand of the polynucleotide of (a); and c) a DNA which would hybridize to the non-coding strand of the polynucleotide of (a) but for the redundancy of the genetic code. Polynucleotides of the invention comprise any one of the polynucleotide set out in SEQ ID NO: 18, SEQ ID NO: 20, and SEQ ID NO: 22, as well as fragments thereof The invention provide polynucleotides which are DNA molecules. DNA molecules include cDNA, genomic DNA, and wholly or partially chemically synthesized DNA molecule. The invention also provides antisense polynucleotides which specifically hybridizes with the complement of a polynucleotide of the invention.

The invention also provides expression constructs comprising a polynucleotide of the invention, host cells transformed or transfected with an expression construct of the invention, and methods for producing a PDE10 polypeptide comprising the steps of: a) growing the host cell of the invention under conditions appropriate for expression of the PDE10 polypeptide and b) isolating the PDE10 polypeptide from the host cell or the medium of its growth.

The invention further provides antibodies specifically immunoreactive with a polypeptide of the invention. Preferably, the antibody is a monoclonal antibody. The invention also provides hybridomas which produces an antibody of the invention. Anti-idiotype antibody specifically immunoreactive with the antibody of the invention are also contemplated.

The invention also provides methods to identify a specific binding partner compound of a PDE10 polypeptide comprising the steps of: a) contacting the PDE10 polypeptide with a compound under conditions which permit binding between the compound and the PDE10 polypeptide; b) detecting binding of the compound to the PDE10 polypeptide; and c) identifying the compound as a specific binding partner of the PDE10 polypeptide. Preferably, methods of the invention identify specific binding partners that modulate activity of the PDE10 polypeptide. In one aspect, the methods identify compounds that inhibits activity of the PDE10 polypeptide. In another aspect, the methods identify compounds that enhance activity of the PDE10 polypeptide.

The invention also provides methods to identify a specific binding partner compound of the PDE10 polynucleotide of the invention comprising the steps of: a) contacting the PDE10 polynucleotide with a compound under conditions which permit binding between the compound and the PDE10 polynucleotide; b) detecting binding of the compound to the PDE10 polynucleotide; and c) identifying the compound as a specific binding partner of the PDE10 polynucleotide. Preferably, the methods identify specific binding partner compounds that modulate expression of a PDE10 polypeptide encoded by the PDE10 polynucleotide. In one aspect, method of the invention identify compounds that inhibit expression of the PDE10 polypeptide. In another aspect, methods of the invention identify compounds that enhance expression of the PDE10 polypeptide.

Binding partner compounds identified by methods of the invention are also contemplated, as are compositions comprising the compound. The invention further comprehends use of binding partner compounds of the invention in production of medicaments for the treatment of PDE10-related disorders.

DETAILED DESCRIPTION OF THE INVENTION

The present invention provides polypeptides and underlying polynucleotides for a novel PDE family designated PDE10. The PDE10 family is distinguished from previously known PDE families in that it shows a lower degree of sequence homology than would be expected for a member of a known family of PDEs and it is not sensitive to inhibitors that are known to be specific for previously identified PDE families. Outside of the catalytic region of the protein, PDE10 shows little homology to other known PDEs. Even over the catalytic region, PDE10 amino acid sequence identity is less than 40% when compared with the same region in known PDEs. The invention includes both naturally occurring and non-naturally occurring PDE10 polynucleotides and polypeptide products thereof Naturally occurring PDE10 products include distinct gene and polypeptide species within the PDE10 family; these species include those which are expressed within cells of the same animal as well as corresponding species homologs expressed in cells of other animals. Within each PDE10 species, the invention further provides splice variants encoded by the same polynucleotide but which arise from distinct mRNA transcripts. Non-naturally occurring PDE10 products include variants of the naturally occurring products such as analogs (i.e., wherein one or more amino acids are added, substituted, or deleted) and those PDE10 products which include covalent modifications (i.e., fusion proteins, glycosylation variants, and the like).

The present invention provides novel purified and isolated polynucleotides (e.g., DNA sequences and RNA transcripts, both sense and complementary antisense strands, including splice variants thereof) encoding human PDE10s. DNA sequences of the invention include genomic and cDNA sequences as well as wholly or partially chemically synthesized DNA sequences. Genomic DNA of the invention comprises the protein coding region for a polypeptide of the invention and includes allelic variants of the preferred polynucleotide of the invention. Genomic DNA of the invention is distinguishable from genomic DNAs encoding polypeptides other than PDE10 in that it includes the PDE10 coding region as defined by PDE10 cDNA of the invention. The invention therefore provides structural, physical, and functional characterization for genomic PDE10 DNA. Allelic variants are known in the art to be modified forms of a wild type gene sequence, the modification resulting from recombination during chromosomal segregation or exposure to conditions which give rise to genetic mutation. Allelic variants, like wild type genes, are inherently naturally occurring sequences (as opposed to non-naturally occurring variants which arise from in vitro manipulation). "Synthesized," as used herein and is understood in the art, refers to purely chemical, as opposed to enzymatic, methods for producing polynucleotides. "Wholly" synthesized DNA sequences are therefore produced entirely by chemical means, and "partially" synthesized DNAs embrace those wherein only portions of the resulting DNA were produced by chemical means. A preferred DNA sequence encoding a human PDE10 polypeptide is set out in SEQ ID NO: 1. The worker of skill in the art will readily appreciate that the preferred DNA of the invention comprises a double stranded molecule, for example the molecule having the sequence set forth in SEQ ID NO: 1 along with the complementary molecule (the "non-coding strand" or "complement") having a sequence deducible from the sequence of SEQ ID NO: 1 according to Watson-Crick base paring rules for DNA. Also preferred are polynucleotides encoding the PDE10 polypeptide of SEQ ID NO: 2.

The disclosure of a full length polynucleotide encoding a PDE10 polypeptide makes readily available to the worker of ordinary skill in the art every possible fragment of the full length polynucleotide. The invention therefore provides fragments of PDE10-encoding polynucleotides of the invention comprising at least 10 to 20, and preferably at least 15, nucleotides, however, the invention comprehends fragments of various lengths. Preferably, fragment polynucleotides of the invention comprise sequences unique to the PDE10-encoding polynucleotide sequence, and therefore hybridize under stringent or preferably moderate conditions only (i.e., "specifically") to polynucleotides encoding PDE10, or PDE10 polynucleotide fragments containing the unique sequence. Polynucleotide fragments of genomic sequences of the invention comprise not only sequences unique to the coding region, but also include fragments of the full length sequence derived from introns, regulatory regions, and/or other non-translated sequences. Sequences unique to polynucleotides of the invention are recognizable through sequence comparison to other known polynucleotides, and can be identified through use of alignment programs made available in public sequence databases.

The invention also provides fragment polynucleotides that are conserved in one or more polynucleotides encoding members of the PDE10 family of polypeptides. Such fragments include sequences characteristic of the family of PDE10 polynucleotides, and are also referred to as "signature sequences." The conserved signature sequences are readily discernable following simple sequence comparison of polynucleotides encoding members of the PDE10 family. Fragments of the invention can be labeled in a manner that permits their detection, and radioactive and non-radioactive labeling are comprehended.

Fragment polynucleotides are particularly useful as probes for detection of full length or other fragment PDE10 polynucleotides. One or more fragment polynucleotides can be included in kits that are used to detect the presence of a polynucleotide encoding PDE10, or used to detect variations in a polynucleotide sequence encoding PDE10.

The invention further embraces species homologs, preferably mammalian, of the human PDE10 DNA. The polynucleotide sequence information provided by the invention makes possible the identification and isolation of polynucleotides encoding related mammalian PDE10 molecules by well known techniques including Southern and/or Northern hybridization, and polymerase chain reaction (PCR). Examples of related polynucleotides include human and non-human genomic sequences, including allelic variants, as well as polynucleotides encoding polypeptides homologous to PDE10 and structurally related polypeptides sharing one or more biological, immunological, and/or physical properties of PDE10.

The invention also embraces DNA sequences encoding PDE10 species which hybridize under moderately stringent conditions to the non-coding strands, or complements, of the polynucleotide in any one of SEQ ID NOs: 1, 18, 20, and 22. DNA sequences encoding PDE10 polypeptides which would hybridize thereto but for the redundancy of the genetic code are contemplated by the invention. Exemplary moderate hybridization conditions are as follows: hybridization at 65° C. in 3×SSC, 0.1% Sarkosyl, and 20 mM sodium phosphate, pH 6.8, and washing at 65° C. in 2×SSC with 0.1% SDS. Exemplary high stringency conditions would include a final wash in 0.2×SSC/0.1% SDS, at 65° C. to 75° C. It is understood in the art that conditions of equivalent stringency can be achieved through variation of temperature and buffer, or salt concentration as described Ausebel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

Autonomously replicating recombinant expression constructions such as plasmid and viral DNA vectors incorporating PDE10 sequences are also provided. Expression constructs wherein PDE10-encoding polynucleotides are operatively-linked to an endogenous or exogenous expression control DNA sequence and a transcription terminator are also provided.

According to another aspect of the invention, host cells are provided, including procaryotic and eucaryotic cells, either stably or transiently transformed with DNA sequences of the invention in a manner which permits expression of PDE10 polypeptides of the invention. Expression systems of the invention include bacterial, yeast, fungal, viral, invertebrate, and mammalian cells systems. Host cells of the invention are a valuable source of immunogen for development of antibodies specifically immunoreactive with PDE10. Host cells of the invention are also conspicuously useful in methods for large scale production of PDE10 polypeptides wherein the cells are grown in a suitable culture medium and the desired polypeptide products are isolated from the cells or from the medium in which the cells are grown by, for example, immunoaffinity purification.

Knowledge of PDE10 DNA sequences allows for modification of cells to permit, or increase, expression of endogenous PDE10. Cells can be modified (e.g., by homologous recombination) to provide increased PDE10 expression by replacing, in whole or in part, the naturally occurring PDE10 promoter with all or part of a heterologous promoter so that the cells express PDE10 at higher levels. The heterologous promoter is inserted in such a manner that it is operatively-linked to PDE10 encoding sequences. See, for example, PCT International Publication No. WO 94/12650, PCT International Publication No. WO 92/20808, and PCT International Publication No. WO 91/09955. The invention also comprehends that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the PDE10 coding sequence, amplification of the marker DNA by standard selection methods results in co-amplification of the PDE10 coding sequences in the cells.

The DNA sequence information provided by the present invention also makes possible the development through, e.g homologous recombination or "knock-out" strategies [Capecchi, *Science* 244:1288–1292 (1989)], of animals that fail to express functional PDE10 or that express a variant of PDE10. Such animals are useful as models for studying the in vivo activities of PDE10 and modulators of PDE10.

The invention also provides purified and isolated mammalian PDE10 polypeptides as set out in SEQ ID NOs: 2, 19, 21, and 23. Presently preferred is a PDE10 polypeptide comprising the amino acid sequence set out in SEQ ID NO: 2. The invention embraces PDE10 polypeptides encoded by a DNA selected from the group consisting of: a) the DNA sequence set out in SEQ ID NOs: 1, 18, 20, or 22; b) a DNA molecule which hybridizes under stringent conditions to the noncoding strand of the protein coding portion of (a); and c) a DNA molecule that would hybridize to the DNA of (a) but for the degeneracy of the genetic code. The invention also embraces polypeptide fragments of the sequences set out in SEQ ID NOs: 2, 19, 21, or 23 wherein the fragments maintain biological or immunological properties of a PDE10 polypeptide. Preferred polypeptide fragments display antigenic properties unique to or specific for the PDE10 family of polypeptides. Fragments of the invention can be prepared by any the methods well known and routinely practiced in the art, having the desired biological and immunological properties.

The invention embraces polypeptides have at least 99%, at least 95%, at least 90%, at least 85%, at least 80%, at least 75%, at least 70%, at least 65%, at least 60%, at least 55% and at least 50% identity and/or homology to the preferred PDE10 polypeptide on the invention. Percent amino acid sequence "identity" with respect to the preferred polypeptide of the invention is defined herein as the percentage of amino acid residues in the candidate sequence that are identical with the residues in the PDE10 sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the PDE10 sequence after aligning the sequences and introducing gaps, if necessary, to achieve the maximum percent sequence identity, and also considering any conservative substitutions as part of the sequence identity. Conservative substitutions can be defined as set out below.

PDE10 polypeptides of the invention may be isolated from natural cell sources or may be chemically synthesized, but are preferably produced by recombinant procedures involving host cells of the invention. Use of various host cells is expected to provide for such post-translational modifications (e.g., glycosylation, truncation, lipidation, and phosphorylation) as may be needed to confer optimal biological activity on recombinant expression products of the invention. PDE10 products of the invention may be full length polypeptides, biologically or immunologically active fragments, or variants thereof which retain specific PDE10 biological or immunological activity. Variants may comprise PDE10 polypeptide analogs wherein one or more of the specified (i.e., naturally encoded) amino acids is deleted or replaced or wherein one or more non-specified amino acids are added: (1) without loss of one or more of the biological activities or immunological characteristics specific for PDE10; or (2) with specific disablement of a particular biological activity of PDE10.

Variant products of the invention include mature PDE10 products, i.e., PDE10 products wherein leader or signal sequences are removed, and having additional, non-naturally occurring, amino terminal residues. PDE10 products having an additional methionine residue at position $^{-1}$ (Met$^{-1}$-PDE10) are contemplated, as are PDE10 products having additional methionine and lysine residues at positions −2 and −1 (Met$^{-2}$-Lys$^{-1}$-PDE10). Variants of these types are particularly useful for recombinant protein production in bacterial cell types.

The invention also embraces PDE10 variants having additional amino acid residues that result from use of specific expression systems. For example, use of commercially available vectors that express a desired polypeptide such as a glutathione-S-transferase (GST) fusion product provide the desired polypeptide having an additional glycine residue at position −1 as a result of cleavage of the GST component from the desired polypeptide. Variants which result from expression in other vector systems are also contemplated.

Variant polypeptides include those wherein conservative substitutions have been introduced by modification of polynucleotides encoding polypeptides of the invention. Conservative substitutions are recognized in the art to classify amino acids according to their related physical properties and can be defined as set out in Table I (from WO 97/09433, page 10, published Mar. 13, 1997 (PCT/GB96/02197, filed Sep. 6, 1996).

TABLE I

Conservative Substitutions I

| SIDE CHAIN CHARACTERISTIC | | AMINO ACID |
| --- | --- | --- |
| Aliphatic | Non-polar | G A P |
| | | I L V |
| | Polar-uncharged | C S T M |
| | | N Q |
| | Polar-charged | D E |
| | | K R |
| Aromatic | | H F W Y |
| Other | | N Q D E |

Alternatively, conservative amino acids can be grouped as defined in Lehninger, [*Biochemistry*, Second Edition; Worth Publishers, Inc. New York:N.Y. (1975), pp.71–77] as set out in Table II.

TABLE II

Conservative Substitutions II

| SIDE CHAIN CHARACTERISTIC | AMINO ACID |
| --- | --- |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

The invention further embraces PDE10 products modified to include one or more water soluble polymer attachments. Particularly preferred are PDE10 products covalently modified with polyethylene glycol (PEG) subunits. Water soluble polymers may be bonded at specific positions, for example at the amino terminus of the PDE10 products, or randomly attached to one or more side chains of the polypeptide.

Also comprehended by the present invention are antibodies (e.g., monoclonal and polyclonal antibodies, single chain antibodies, chimeric antibodies, human antibodies CDR-grafted antibodies, or otherwise "humanized" antibodies, antigen binding antibody domains including Fab, Fab', F(ab')$_2$, F$_v$, or single variable domains, and the like) and other binding proteins specific for PDE10 products or fragments thereof. Specific binding proteins can be developed using isolated or recombinant PDE10 products, PDE10 variants, or cells expressing such products. The term "specific for" indicates that the variable regions of the antibodies recognize and bind PDE10 polypeptides exclusively (i.e., able to distinguish PDE10 polypeptides from the superfamily of PDE polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (eds), *Antibodies: A Laboratory Manual*; Cold Spring Harbor Laboratory; Cold Spring Harbor, N.Y. (1988), Chapter 6. Antibodies that recognize and bind fragments of the PDE10 polypeptides of the invention are also contemplated, provided that the antibodies are first and foremost specific for, as defined above, PDE10 polypeptides. As with antibodies that are specific for full length PDE10 polypeptides, antibodies of the invention that recognize PDE10 fragments are those which can distinguish PDE10 polypeptides from the superfamily of PDE polypeptides despite inherent sequence identity, homology, or similarity found in the family of proteins.

Binding proteins are useful for purifying PDE10 products and detection or quantification of PDE10 products in fluid and tissue samples using known immunological procedures. Binding proteins are also manifestly useful in modulating (i.e., blocking, inhibiting or stimulating) biological activities of PDE10, especially those activities involved in signal transduction. Anti-idiotypic antibodies specific for anti-PDE10 antibodies are also contemplated.

The scientific value of the information contributed through the disclosures of DNA and amino acid sequences of the present invention is manifest. As one series of examples, knowledge of the sequence of a cDNA for PDE10 makes possible through use of Southern hybridization or polymerase chain reaction (PCR) the identification of genomic DNA sequences encoding PDE10 and PDE10 expression control regulatory sequences such as promoters, operators, enhancers, repressors, and the like. DNA/DNA hybridization procedures carried out with DNA sequences of the invention under moderately to highly stringent conditions are likewise expected to allow the isolation of DNAs encoding allelic variants of PDE10; allelic variants are known in the art to include structurally related proteins sharing one or more of the biochemical and/or immunological properties specific to PDE10. Similarly, non-human species genes encoding proteins homologous to PDE10 can also be identified by Southern and/or PCR analysis and useful in animal models for PDE10-related disorders. As an alternative, complementation studies can be useful for identifying other human PDE10 products as well as non-human proteins, and DNAs encoding the proteins, sharing one or more biological properties of PDE10.

Polynucleotides of the invention are also useful in hybridization assays to detect the capacity of cells to express PDE10. Polynucleotides of the invention may also be the basis for diagnostic methods useful for identifying a genetic alteration(s) in a PDE10 locus that underlies a disease state or states.

The DNA and amino acid sequence information provided by the present invention also makes possible the systematic analysis of the structure and function of PDE10 s. DNA and amino acid sequence information for PDE10 also permits identification of binding partner compounds with which a PDE10 polypeptide or polynucleotide will interact. Binding partner compounds include proteins and non-protein compounds such as small molecules. Agents that modulate (i.e., increase, decrease, or block) PDE10 activity or expression may be identified by incubating a putative modulator with a PDE10 polypeptide or polynucleotide and determining the effect of the putative modulator on PDE10 phosphodiesterase activity or expression. The selectivity of a compound that modulates the activity of the PDE10 can be evaluated by comparing its binding activity on the PDE10 to its activity on other PDE enzymes. Cell based methods, such as di-hybrid assays to identify DNAs encoding binding compounds and split hybrid assays to identify inhibitors of PDE10 polypeptide interaction with a known binding polypeptide, as well as in vitro methods, including assays wherein a PDE10 polypeptide, PDE10 polynucleotide, or a binding partner are immobilized, and solution assays are contemplated under the invention.

Selective modulators may include, for example, antibodies and other proteins or peptides which specifically bind to a PDE10 polypeptide or a PDE10-encoding nucleic acid, oligonucleotides which specifically bind to a PDE10 polypeptide or a PDE10 gene sequence, and other non-peptide compounds (e.g, isolated or synthetic organic and inorganic molecules) which specifically react with a PDE10 polypeptide or underlying nucleic acid. Mutant PDE10 polypeptides which affect the enzymatic activity or cellular localization of the wild-type PDE10 polypeptides are also contemplated by the invention. Presently preferred targets for the development of selective modulators include, for example: (1) regions of the PDE10 polypeptide which contact other proteins and/or localize the PDE10 polypeptide within a cell, (2) regions of the PDE10 polypeptide which bind substrate, (3) cyclic nucleotide-binding site(s) of the PDE10 polypeptide, (4) phosphorylation site(s) of the PDE10 polypeptide and (5) regions of the PDE10 polypeptide which are involved in multimerization of PDE10 subunits. Still other selective modulators include those that recognize specific PDE10 encoding and regulatory polynucleotide sequences. Modulators of PDE10 activity may be therapeutically useful in treatment of a wide range of diseases and physiological conditions in which PDE activity is known to be involved.

PDE10 polypeptides of the invention are particularly amenable to use in high throughput screening assays to identify binding partners, and preferably modulators. Cell based assays are contemplated, including yeast based assay systems as well as mammalian cell expression systems as described in Jayawickreme and Kost, *Curr. Opin. Biotechnol.* 8:629–634 (1997). Alternatively, automated and minaturized high throughput screening (HTS)assays, such as high density free format high density screening, as described in Houston and Banks, *Curr. Opin. Biotehcnol.* 8:734–740 (1997). Combinatorial libraries are particularly useful in high throughput screening assays.

There are a number of different libraries used for the identification of small molecule modulators, including, (1) chemical libraries, (2) natural product libraries, and (3) combinatorial libraries comprised of random peptides, oligonucleotides or organic molecules.

Chemical libraries consist of structural analogs of known compounds or compounds that are identified as "hits" or "leads" via natural product screening. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) variants thereof. For a review, see *Science* 282:63–68 (1998). Combinatorial libraries are composed of large numbers of peptides, oligonucleotides, or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include protein, peptidomimetic, multiparallel synthetic collection, recombinatorial, and polypeptide libraries. For a review of combinatorial chemistry and libraries created therefrom, see Myers, *Curr. Opion. Biolechnol.* 8:701–707 (1997). Identification of modulators through use of the various libraries described herein permits modification of the candidate "hit" (or "lead") to optimize the capacity of the "hit" to modulate activity.

Also made available by the invention are anti-sense polynucleotides which recognize and hybridize to polynucleotides encoding PDE10. Full length and fragment anti-sense polynucleotides are provided. The worker of ordinary skill will appreciate that fragment anti-sense molecules of the invention include (i) those which specifically recognize and hybridize to PDE10 RNA (as determined by sequence comparison of DNA encoding PDE10 to DNA encoding other known molecules) as well as (ii) those which recognize and hybridize to RNA encoding variants in the PDE10 family of proteins. Antisense polynucleotides that hybridize to RNA encoding other members of the PDE10 family of proteins are also identifiable through sequence comparison to identify characteristic, or signature, sequences for the family of molecules. Anti-sense polynucleotides are particularly relevant to regulating expression of PDE10 by those cells expressing PDE10 mRNA.

Antisense nucleic acids (preferably 10 to 20 base pair oligonucleotides) capable of specifically binding to PDE10 expression control sequences or PDE10 RNA are introduced into cells (e.g., by a viral vector or colloidal dispersion system such as a liposome). The antisense nucleic acid binds to the PDE10 target nucleotide sequence in the cell and prevents transcription or translation of the target sequence. Phosphorothioate and methylphosphonate antisense oligonucleotides are specifically contemplated for therapeutic use according to the invention. The antisense oligonucleotides may be further modified by poly-L-lysine, transferrin polylysine, or cholesterol moieties at the 5' end.

The invention further comprehends methods to modulate PDE10 expression through use of ribozymes. For a review, see Gibson and Shillitoe, *Mol. Biotech.* 7:125–137 (1997). Ribozyme technology can be utilized to inhibit translation of PDE10 MRNA in a sequence specific manner through (i) the hybridization of a complementary RNA to a target mRNA and (ii) cleavage of the hybridized mRNA through nuclease activity inherent to the complementary strand. Ribozymes can identified by empirical methods but more preferably are specifically designed based on accessible sites on the target mRNA [Bramlage, et al., *Trends in Biotech* 16:434–438 (1998).] Delivery of ribozymes to target cells can be accomplished using either exogenous or endogenous delivery techniques well known and routinely practiced in the art. Exogenous delivery methods can include use of targeting liposomes or direct local injection. Endogenous methods include use of viral vectors and non-viral plasmids.

Ribozymes can specifically modulate expression of PDE10 when designed to be complementary to regions unique to a polynucleotide encoding PDE10. "Specifically modulate" therefore is intended to mean that ribozymes of the invention recognizes only a polynucleotide encoding PDE10. Similarly, ribozymes can be designed to modulate expression of all or some of the PDE10 family of proteins. Ribozymes of this type are designed to recognize polynucleotide sequences conserved in all or some of the polynucleotides which encode the family of proteins.

The invention further embraces methods to modulate transcription of PDE10 through use of oligonucleotide-directed triplet helix formation. For a review, see Lavrovsky, et al., *Biochem. Mol. Med.* 62:11–22 (1997). Triplet helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Preferred target sequences for hybridization include promoter and enhancer regions to permit transcriptional regulation of PDE10 expression. Oligonucleotides which are capable of triplet helix formation are also useful for site-specific covalent modification of target DNA sequences. Oligonucleotides useful for covalent modification are coupled to various DNA damaging agents as described in Lavrovsky, et al. [supra].

The invention comprehends mutations in the PDE10 gene that result in loss of normal function of the PDE10 gene product and underlie human disease states in which failure of the PDE10 is involved. Gene therapy to restore PDE10 activity would thus be indicated in treating those disease states. Delivery of a functional PDE10 gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature*, supplement to vol. 392, no. 6679, pp.25–20 (1998). For additional reviews of gene therapy technology see Friedmann, *Science*, 244: 1275–1281 (1989); Verma, *Scientific American*: 68–84 (1990); and Miller, *Nature*, 357: 455–460 (1992). Alternatively, it is contemplated that in other human disease states, preventing the expression of or inhibiting the activity of PDE10 will be useful in treating the disease states. It is contemplated that antisense therapy or gene therapy could be applied to negatively regulate the expression of PDE10.

Identification of modulators of PDE10 expression and/or biological activity provides methods to treat disease states that arise from aberrant PDE10 activity. Modulators may be prepared in compositions for administration, and preferably include one or more pharmaceutically acceptable carriers, such as pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma. The modulator compositions can be packaged in forms convenient for delivery. The compositions can be enclosed within a capsule, sachet, cachet, gelatin, paper, or other container. These delivery forms are preferred when compatible with entry of the composition into the recipient organism and, particularly, when the composition is being delivered in unit dose form. The dosage units can be packaged, e.g., in tablets, capsules, suppositories or cachets. The compositions may be introduced into the subject by any conventional method including, e.g., by intravenous, intradermal, intramuscular, intramarnmary, intraperitoneal, or subcutaneous injection; by oral, sublingual, nasal, anal, vaginal, or transdermal delivery; or by surgical implantation, e.g., embedded under the splenic capsule or in the cornea. The treatment may consist of a single dose or a plurality of doses over a period of time.

The invention also embraces use of a PDE10 polypeptide, a PDE10 polynucleotide, or a binding partner thereof in production of a medicament for treatment of a PDE10-related biological disorder.

The present invention is illustrated by the following examples relating to the isolation of a polynucleotide encoding a PDE10 polypeptide and expression thereof Example 1 describes identification of an EST encoding a partial PDE10 polypeptide and isolation of a full length PDE10-encoding clone. Example 2 relates to Northern blot analysis of PDE10 expression. Example 3 addresses chromosome mapping of PDE10. Example 4 describes expression and characterization of a recombinant PDE10 polypeptide. Example 5 describes production of anti-PDE10 antibodies. Example 6 provides an analysis of PDE10 expression using in situ hybridization. Example 7 relates to high throughput screening to identify inhibitors of PDE10.

EXAMPLE 1

Identification of an EST Related to a Human PDE and Isolation of a Full Length PDE10-encoding Polynucleotide Using the sequences of known human, 3', 5' cyclic nucleotide phosphodiesterases, a search of the National Center for Biotechnology Information (NCBI) Expressed Sequence Tags (EST) database was undertaken in order to identify cDNA fragments that could potentially be useful for the identification of novel phosphodiesterase (PDE) genes. This database contains DNA sequences representing one or both ends of cDNAs collected from a variety of tissue sources. A single sequencing run is performed on one or both ends of the cDNA and the quality of the DNA sequence varies tremendously. At the time the PDE searches were performed, the EST sequence database contained more than 600,000 cDNA sequences from a variety of organisms.

The search for novel PDE sequences included three steps. First, the BLASTN program available through NCBI was used to identify DNA sequences in the EST sequence database with homology to cDNA sequences encoding known human PDEs. The program compares a nucleotide query sequence against a nucleotide sequence database. The cDNA sequences of the fifteen known human PDEs were submitted and fifteen BLASTN searches were performed; the query PDE sequences included PDE1A3 [Loughney, et al., *J. Biol. Chem.* 271:796–806 (1996)], PDE1B1 [Yu, et al., *Cell Signaling*, 9:519–529 (1997)], PDE1C2 [Loughney, et al., *J. Biol. Chem.* 271:796–806 (1996)], PDE2A3 [Rosman, et al., *Gene* 191:89–95 (1997)], PDE3A [Meacci, et al., *Proc. Natl. Acad. Sci. (USA)* 89:3721–3725 (1992)], PDE3B [Miki et al., *Genomics* 36:476–485 (1996)], PDE4A5 [Bolger, et al., *Mol. Cell. Biol.* 13:6558–6571 (1993)], PDE4B2 [Bolger, et al., *Mol. Cell. Biol.* 13:6558–6571 (1993)], PDE4C [Bolger, et al., *Mol. Cell. Biol.* 13:6558–6571 (1993)], PDE4D1 [Bolger, et al., *Biochem. J.* 328:539–548 (1997)] and PDE4D3 [Bolger, et al., *Mol. Cell. Biol.* 13:6558–6571 (1993)], PDE5A, PDE6A [Pittler, et al., *Genomics* 6:272–283 (1990)], PDE6B [Collins, et al., *Genomics* 13:698–704 (1992)], PDE6C [Piriev, et al., *Genomics* 28:429–435 (1995), and PDE7A1 [Michaeli, et al., *J. Biol. Chem.* 17:12925–12932 (1993)]. The BLASTN results were examined and EST sequences that were judged as corresponding to each of the fifteen known PDE cDNAs were identified and collected into a table. The PDE6A and PDE6B sequences used as queries were truncated at 3' end (removing a portion of the 3' untranslated region) due to the presence of repetitive elements in the 3' untranslated region of the cDNAs.

Secondly, the NCBI TBLASTN program was used to examine the homology between the protein sequence of the fifteen known human PDEs (as above) and the six different possible proteins encoded by each of the EST DNA sequences. In this search, the EST sequences are translated in the six possible reading frames and the amino acid sequences generated are compared to the query PDE amino acid sequences. Sequences identified as homologous at the amino acid level were examined and any EST sequences positively identified as corresponding to a known PDE during the BLASTN search described above were discarded.

The third step of the search involved analyzing the sequences that were not known PDEs. These amino acid sequences were homologous to a known PDE but were not identified as one of the 15 known PDE genes during the BLASTN searches.

The initial BLAST searches identified three EST sequences, designated X88347 (SEQ ID NO: 3), X88467 (SEQ ID NO: 4), and X88465 (SEQ ID NO: 5), that were obtained from an exon trapping experiment using chromosome 21 genomic DNA and found to encode an amino acid sequence having homology to the catalytic region of one or more of the PDE query sequences. X88347 showed homology with the amino acid sequences of PDE1A, 1B, 1C, 3A, 3B, 4A, 4B and 4D; X88467 showed homology to PDE1A, 1B, 1C, 4A, 4B, 4C, and D4; and X88465 was homologous to PDE1A and 1B amino acid sequences. At the 5' terminus, EST X88465 was 58 nucleotides shorter than was X88467 and was not considered further.

When X88347 was translated from nucleotides 1–222 and the resultant protein was compared to PDE1A, the two proteins were the same at 23 of 51 amino acid positions (45% identity). When X88467 was translated from nucleotide 3 to 155 and the resultant protein compared to PDE1A, 15 of 36 amino acids were the same (42% identity). Because ESTs X88347 and X88467 showed homology to two different regions of the catalytic region of PDE1A, it seemed possible that they represented two different exons from a novel PDE gene.

X88347 was used as a query in a BLASTN search of the NCBI EST database. In addition to itself, X88347 identified three other human EST sequences with high enough homology to suggest the sequences were derived from the same gene. EST R00718 (SEQ ID NO: 6) showed 91% identity to X88347. R00719 (SEQ ID NO: 7) represented the 3'-end of the same cDNA as R00718. R45187 (SEQ ID NO: 8) showed 88% identity to X88347. Two mouse cDNAs were also identified; W82786 (SEQ ID NO: 9)(91% identity) and W10517 (SEQ ID NO: 10) appeared to represent the mouse homolog of X88347. A BLASTN search using W10517 as probe identified another sequence H90802 (SEQ ID NO: 11), which appeared to represent another human EST that may be part of the human PDE gene. The several human cDNAs were not identical to each other, and the quality of the sequencing was poor. The cDNA represented by the R00719 and R00718 EST sequences was obtained from the American Type Culture Collection (Rockville, Md.) which maintains and makes publicly available deposits of ESTs identified and sequenced by I.M.A.G.E., Lawrence Livermore National Laboratory, (Livermore, Calif.). The cDNA had been isolated from a fetal liver and spleen library and mapped to chromosome 21.

R00718/9 was sequenced upon receipt and found to be consistent with the EST database sequence. The polynucleotide and amino acids sequences for R00718/9 are set out in SEQ ID Nos: 12 and 13, respectively. The R00718/9 clone contained a 0.6 kb insert with a poly A tail at the 3'-end. The open reading frame encoded a protein with homology to other PDEs but did not extend to the 5'end of the cDNA. Beginning at amino acid position 9, a QSDRE sequence was found. Corresponding D and E residues were found within all of the query sequences. Query sequences also included a conserved E(F/Y) sequence located amino terminal to the conserved D and E residues, but this sequence was not found in EST R00718/9. Instead, the EST contained eight amino acids followed by a stop codon. The R00718/9 cDNA appeared to diverge from the PDE query sequences in the catalytic region and the open reading frame was not maintained. The disrupted open reading frame may suggest the presence of an intron that had not been removed or that the R00718/9 sequence was joined to some unidentified extraneous polynucleotide sequence. The gene represented by R00718/9 was designated PDE10.

In order to identify additional PDE10 sequences, a probe was generated based on the PDE10 sequence and used to screen cDNA libraries. First, two primers, R71S100R (SEQ ID NO: 14) and R71A521H (SEQ ID NO: 15) were synthesized for use in PCR to amplify a 420 nucleotide portion of the R00718/9 DNA fragment (nucleotides 130 to 550). Primer R71S100R generated an EcoRI restriction site in the amplification product (underlined below) and primer R71A521H generated a HindIII site (also underlined below). The PCR fragment was designed to include the region of R00718/9 homologous to other PDEs, but not the poly A tail.

```
R71S100R                             (SEQ ID NO: 14)
    AGTCGAATTCACCGTGAGAAGTCAGAAG
R71A521H                             (SEQ ID NO: 15)
    GTCAAAGCTTACATGGTCTTGTGGTGCC
```

The PCR reaction contained 50 pg R00719 cDNA, 10 ng/µl each primer, 0.2 mM dNTP, 1× PCR buffer (Perkin-Elmer), 2 mM $MgCl_2$, and 1.25 U Taq polymerase (Perkin-Elmer). The reaction was first maintained at 94° C. for four minutes, after which thirty cycles of one minute 94° C., two minutes 50° C., and four minutes at 72° C. were performed. The PCR fragment was purified using low melting point agarose gel electrophoresis.

For library screening, the PCR fragment was labeled with $^{32}P$ with a random priming kit (Boehringer Mannheim) according to manufacturer's instructions and used to screen $10^6$ cDNAs from a human heart cDNA library (Stratagene, La Jolla, Calif.), $5\times10^5$ cDNAs from a human hippocampal cDNA library (Clontech, Palo Alto, Calif.), and $7.5\times10^5$ cDNAs from a human fetal brain cDNA library (Stratagene). Hybridization was carried out overnight in buffer containing 3×SSC, 0.1% Sarkosyl, 20 mM sodium phosphate, pH 6.8, 10× Denhardt's solution, and 50 µg/ml salmon sperm DNA at 65° C. Eleven positives were obtained from the fetal brain library and three from the hippocampal library. Partial sequencing led to the selection of one, FB79c, for further characterization. The polynucleotide and deduced amino acid sequences for FB79c are set out in SEQ ID NOs: 16 and 17, respectively.

FB79c contained a 1.3 kb insert; the 3'end of FB79c extended further than that of R00718/9 and contained 12 adenosine residues of the poly A tail of R00718/9, an EcoRI site (GGAATTC), an additional fifty-nine nucleotides and a poly A sequence. At the 5'end, the sequence for FB79c differed from that of R00718/9 beginning at, and continuing 5' of, nucleotide 121 of R00718/9 (corresponding to nucleotide 744 of FB79c). The open reading frame in FB79c (encoding a protein with homology to the query PDEs) did not extend to the 5'end of the cDNA but ended in a stop codon at nucleotide 104.

A sequence within the FB79c DNA located upstream of the point of divergence from R00718/9 (but within the portion of the open reading frame with homology to the other PDEs ) was the region chosen for a probe in subsequent library screening. The isolated sequence selected was a 0.36 kb EcoRV fragment extending from nucleotide 308 to nucleotide 671 of FB79c and was used to screen $1.75\times10^6$ cDNAs from the fetal brain cDNA library (Stratagene). More than twenty cDNAs were identified and twelve were subjected to partial restriction mapping and DNA sequencing. More extensive sequencing on six of them led to the selection of clones FB76.2 and FB68.2 for complete sequencing. The polynucleotide and amino acid sequences for clone FB76.2 are set out in SEQ ID NOs: 18 and 19, respectively, and the polynucleotide and amino acid sequences for clone FB68.2 are set out in SEQ ID NOs. 20 and 21, respectively.

FB76.2 contained a 1.9 kb cDNA insert; the 3'end of the cDNA stopped one nucleotide short of the poly A tail found in clone FB79c and the sequence diverged from FB79c 5' of nucleotide 109 in clone FB79c (corresponding to nucleotide 715 in FB76.2). The open reading frame in the FB76.2 sequence that encoded a protein with homology to the PDE query sequences extended to the 5 'end of the cDNA and the first methionine was encoded beginning at nucleotide 74. Assuming this residue to be the initiating methionine, the open reading frame of FB76.2 encoded a 533 amino acid protein with a predicted molecular weight of 61,708 Da.

Clone FB68.2 contained a 2 kb cDNA insert. At the 3 'end, it extended to the poly A tail found in the FB79c sequence and the open reading frame extended to the 5'end of the cDNA. FB68.2 differed from FB76.2 by the presence of an additional internal 180 nucleotides (nucleotides 225 to 404 of FB68.2) following corresponding nucleotide 335 of FB76.2. Since the number of additional nucleotides in the FB68.2 insertion was divisible by three, it did not alter the reading frame as compared to FB76.2. The position of the insert with respect to maintaining the same reading frame suggested that the sequence might represent an exon found in some, but not all, PDE10 cDNAs. Alternatively, the additional sequence could be an intron that had not been removed from the FB68.2 cDNA.

Because the FB76.2 and FB68.2 differed from each other, additional PDE10 DNAs were obtained and analyzed to more accurately define the PDE10 nucleotide sequence. A 5' 0.3 kb EcoRI fragment of FB76.2 (corresponding to nucleotides 1 to 285) was isolated and used as a probe to screen $7.5\times10^5$ cDNAs from the fetal brain cDNA library. Thirty seven positives were obtained, of which nineteen were first characterized with respect to fragment size (insert) that hybridized to the 0.3 kb EcoRI probe. Eight of the nineteen clones were subsequently characterized by partial sequencing. Two clones, FB93a and FB94a, contained 0.5 kb and 1.6 kb EcoRI fragments, respectively, that hybridized and were chosen for complete sequencing. The polynucleotide and amino acid sequences for clone FB93a are set out in SEQ ID NOs: 22 and 23, respectively, and the polynucleotide and amino acid sequences for clone FB94a are set out in SEQ ID NOs: 1 and 2, respectively.

FB93a contained a 1.5 kb insert which did not extend to the 3'end of FB76.2 but was ninety nucleotides longer than FB76.2 at the 5'end. The additional nucleotides encoded a stop codon beginning at position 47 which was in reading frame with the first methionine in FB76.2 described above (nucleotide 164 in FB93a). The position of the stop codon indicated the presence of a complete open reading frame and that FB76.2 probably represented a full length cDNA. Like FB76.2, FB93a did not contain the 180 nucleotide insert that was present in FB68.2.

FB94a contained a 1.5 kb cDNA insert and the 3'end extended almost 0.1 kb beyond the stop codon. The first methionine was encoded beginning at nucleotide 26, and assuming this residue to be the initiating methionine, FB94a encoded a 466 amino acid protein with a predicted molecular weight of 54,367 Da. FB94a differed from FB76.2 and FB93a by absence of a 149 nucleotide region which, if consistent with the sequences for FB76.2 and FB93a, would have been located after nucleotide 42. The absence of the 149 nucleotide sequence produced a putative initiator methionine that is in a different reading frame than that found in FB76.2 and FB93a. Like FB76.2 and FB93a, FB94a did not contain the 180 nucleotide region found in FB68.2.

A search of the EST data base with the FB94a and FB93a sequences identified yet another possible sequence for a PDE10 cDNA. The sequence of EST A158300 lacked both the 149 nucleotide and the 180 nucleotide sequences discussed above. In addition, A158300 also lacked 55 nucleotides immediately 3' to the 180 nucleotide region as found in the FB68.2 sequence. The open reading frame in A158300 extended to the 5'end and the first methionine corresponded to the same one used by FB76.2 and FB93a. The presence of the additional 55 nucleotide deletion from Al 58300 resulted in a different reading frame for the sequence between the site where the 149 nucleotides were deleted and the site where the 180 nucleotides were deleted.

The sequence information for PDE10 derived from these cDNA sequences can be summarized as follows. There is a 149 nucleotide sequence found in some clones (sequences FB76.2, FB93a, FB68.2) but not in all (sequences FB94a, Al 58300). The 149 nucleotide sequence is followed by a 44 nucleotide region that is present in all the PDE10 cDNAs analyzed to date. Following the 44 nucleotide region is a sequence of 235 nucleotides in length. The region can be present in its entirety (as found in the sequence for FB68.2) or without the first 180 nucleotides (as observed in sequences FB76.2 and FB93a). As still another alternative, the whole region can be removed (as found in the sequence for A158300). These possibilities predict six different mRNA structures, four of which have been isolated.

The presence or absence of the 149 nucleotide region may reflect the presence or absence of an exon, and the presence of all or some of the 235 nucleotide region may reflect alternative 3' splice acceptor site usage. As an alternative, it is also possible that the 235 nucleotide region represents two separate exons of 180 and 55 nucleotides in length. The presence or absence of the 149 nucleotide sequence alters the reading frame of the encoded protein as does the presence or absence of the 55 nucleotide sequence.

A number of single nucleotide differences have been observed in comparison of the various PDE10 cDNAs. R00718/9 has a cytosine at nucleotide position 155 whereas the other cDNAs have a thymidine at this position; this difference represented a silent change as proline is encoded by both sequences. R00718/9 also has a cytosine at position 161 whereas the other cDNAs have an adenosine at the same position; this difference also represented a silent change as both sequences encode alanine. FB94a has a guanosine at position 1383 whereas the other cDNAs have an adenosine at this position; as a consequence of the difference, FB94a encodes a glycine rather than a glutamic acid at that position. FB76.2 has an adenosine rather than a cytosine at position 1809; the difference does not effect an amino acid difference since the nucleotide position is located in the 3' untranslated region. FB79c also has one less adenosine in the string of nucleotides between 1204 and 1215 than do the other cDNAs; this difference is also within the 3' untranslated region.

In comparison of a predicted PDE10 amino acid sequence with other known PDEs indicated that most, but not all, of the amino acids that are conserved among the query sequences were also found in PDE10. Comparison of the PDE10 catalytic region to PDE4A, PDE5A, and PDE7A revealed 32%, 30% and 34% identity, respectively.

EXAMPLE 2

Northern Blot

In order to determine which cell and tissue types express PDE10, Northern blot analysis was carried out using a commercially prepared multi-tissue Northern blot (Clontech, Palo Alto, Calif.). The probe was a EcoRI/BclI fragment of the FB76.2 corresponding to nucleotides 1 to 883. Hybridization conditions were as previously described [Loughney et al., supra, (1996)].

Results indicated a 2.2 to 2.4 kb band which was strongest in kidney, present in heart, pancreas, and placenta, and weakest in brain, lung, skeletal muscle and liver. The band was fairly wide in placenta suggesting that it might contain a number of mRNAs of slightly different sizes.

EXAMPLE 3

Chromosome Mapping

As mentioned above, the X88347, X88467, and X88465 ESTs were identified with an exon trapping procedure using DNA from chromosome 21 [Chen et al. 1996]. X88467 was identified as a new sequence with homology to a mouse calcium-, calmodulin-dependent phosphodiesterase Q01065 aa 52-103. XD88347 was identified to be the same as EST R00718 and similar to Drosophila cAMP dependent phosphodiesterase P12252. Both of these sequences were placed in a category described as having strong homology to known protein sequences.

A search of the Sequence Tagged Sites (STS) database at NCBI revealed homology of the 3'-end of PDE10 to STS WI-13322 which has been mapped to region 220.72 cr. from the top of chromosome 21. The cDNA that this STS was derived from begins at nucleotide 1899 of FB68.2, does not have the poly A tail and extends further 3' than FB68.2. It seems likely that this STS sequence represents a PDE10A transcript to which no poly ($A^+$) tail has been added or a PDE10A transcript that uses an alternative site for poly ($A^+$) addition. STS WI-13322 was placed on a Whitehead map of chromosome 21 near SGC35805, which is derived from the gene for the cystathionine beta-synthase (CBS). CBS has been mapped to chromosome 21 at 21q22.3 [Avramopoulos, et al, *Hum. Genet.* 90:566–568 (1993); Munke et al., *Hum. Genet.* 42:550–559 (1988)].

A number of different genetic diseases map to this region of chromosome 21, for example, Down syndrome [Delabar, et al., *Eur. J. Hum. Genet.* 1:114–124(1993)]. It is not clear that PDE10 A falls within the Down syndrome critical region (DSCR) but it is possible that genes elsewhere on chromosome 21 also contribute to Down syndrome [Korenberg, et al., *Proc. Natl. Acad. Sci. (USA)* 91:4997–5001 (1994)]. As another example, a locus involved in bipolar affective disorder in some families has been mapped to 21q22.3 [Vallada, et al., *J.Affect. Disord.* 41:217–221 (1996)]. Other examples include Knobloch syndrome, characterized by myopia and retinal degeneration and detachment [Sertie, et al., *Hum. Mol. Genet.* 5:843–847 (1996)], and one or more genes responsible for congenital recessive deafness (DFNB8, DFNB10) [Veske, et al., *Hum. Mol. Genet.* 5:165168 (1996); Bonne-Tamir, et al., *Am. J. Hum. Genet.* 58:1254–1259 (1996)]. PDE10A may play a role in any or all of these disease states.

EXAMPLE 4

Expression and Characterization of PDE10

The entire open reading frame of the PDE10 cDNA (clone FB94a) was placed into a yeast ADH vector including the alcohol dehydrogenase promoter. The construct was built in two steps.

The 5'end was generated using PCR and FB94a DNA as template. PCR was carried out using the 5' primer below (SEQ ID NO: 25) in combination with 3' primer R71A3 (SEQ ID NO: 26). The 5' primer includes an NcoI site (underlined in SEQ ID NO: 25 below) and the initiating methionine codon of FB94a is in bold. The 5' primer also adds a FLAG® epitope tag (Eastman Kodak, Rochester, N.Y.) to the amino terminus of the encoded protein; the FLAG® tag is an epitope (SEQ ID NO: 24) recognized by the monoclonal antibody M2 (Eastman Kodak).

```
FLAG ® TAG                            (SEQ ID NO: 24)
         Asp-Tyr-Lys-Asp-Asp-Asp-Asp-Lys

5' Primer                             (SEQ ID NO: 25)
         TAGACCATGGACTACAAGGACGACGA-
         TGACAAGATGGACGCATTCAGAAGCACT R71A3                                 (SEQ ID NO: 26)
         CGAGGAGTCAACTTCTTG
```

PCR was carried out using 5 μl each primer (100 μg/ml stock), 5 μl 10× buffer (Perkin Elmer), 5 μl 10× nucleotides (2 mM stock), 3 μl MgCl$_2$ (25 mM stock), FB94a DNA, and 0.3 μl Taq polymerase (Perkin Elmer) in a reaction volume of 50 μl. After incubating the reaction mixture at 94° C. for four minutes, 30 cycles of one minute at 94° C., two minutes at 50° C., and four minutes at 72° C. were carried out. The PCR product was cleaved with NcoI and HincII and purified using agarose gel electrophoresis. The 3' sequence of PDE10 was isolated as a HincII/EcoRI fragment cleaved from FB94a and purified by agarose gel electrophoresis. The two fragments were combined and ligated into a NcoI/EcoRI-digested Bluescript® vector (Stratagene, La Jolla, Calif.), previously modified by the insertion of the ADH promoter previously removed from a YEpC-PADH2d vector [Price et al. *Meth. Enzymol.* 185:308–315 (1990)] as a SacI/NcoI fragment, to generate plasmid PDE10-1. New junctions and sequence generated by PCR were verified by sequencing.

In the second step of plasmid construction, the SacI/SalI fragment from PDE10-1 containing the ADH promoter and PDE10 open reading frame was purified by two rounds of agarose gel electrophoresis and ligated into SacI/SalI cut YEpC-PADH2 vector.

Following transformation into BJ2-54, a yeast strain lacking endogenous PDE activity, a colony was selected, streaked out on SC-leu plates and a single colony carrying the PDE10 construct was chosen for further characterization. Following overnight growth in SC-leu media the culture was diluted 1:250 in fresh SC-leu and grown overnight at 30° C. until it reached a density of $10^7$ cells/ml. The cells were collected by centrifugation, washed once with YEP 3% glycerol media, resuspended in YEP containing 3% glycerol, and grown at 30° C. for another 24 hours. The cells were harvested by centrifugation, washed with water, and frozen at –70° C. until use. Prior to use, an aliquot of the yeast extract was analyzed by SDS PAGE. A protein specific to yeast carrying the PDE10 expression construct that migrated on the SDS PAGE gels with the expected mobility (55.5 kDa) was observed by Coomassie blue staining.

Yeast cells ($1 \times 10^{10}$) were thawed with 200 μg/ml each of pepstatin A, leupeptin, and aprotinin 1 mM DTT, and 20 μg/ml calpain inhibitors (I and II). Two hundred μl of glass beads (0.5 mm, acid washed) were added, and the mixture was vortexed for eight cycles of 30 seconds each. Samples were cooled for 4.5 minutes at 4° C. between cycles. After lysis, 0.8 ml lysis buffer was added, the lysate separated from the beads, and the lysate centrifuged for 30 minutes at 100,000×g in a Beckman TL-100 tabletop centrifuge. The supernatant was aliquoted, frozen in dry ice/ethanol, and stored at –70° C.

Kinetic assays were performed on a BIOMEK® 1000 programmable robotic station (Beckman Instruments). The range of final substrate concentration was 0.2 to 1000 μM for cAMP and 0.6–2000 nM for cGMP. The highest nucleotide concentration contained 1 to 1.5 million Cerenkov counts of $^{32}$P-labeled substrate per assay. The enzyme preparation was initially diluted 1:500 (cAMP as substrate) or 1:50,000 (cGMP as substrate). The enzyme dilution buffer consisted of 25 mM Tris-HCl pH 8.9, 5 μM ZnSO$_4$ 5 mM MgCl$_2$, 0.1 mM DTT, 100 mM NaCl and 0.1 mg/ml BSA (Calbiochem; fatty acid free). Activity at each substrate concentration was derived from a linear fit of successive four-fold enzyme dilutions across the plate.

Assays were performed at 30° C. for 15 minutes. After 12 minutes, 5 μl snake venom from *Crotalus atrox* (15 mg/ml protein) was added to each reaction. Assays were stopped by addition 200 μl of charcoal suspension (25 mg/ml activated charcoal in 0.1 M monobasic potassium phosphate). The plate was centrifuged at 2600 rpm, and 200 μl of each supernatant was transferred into Microbeta® counting plates and counted on a WALLAC Microbeta® by Cerenkov counting. Data were evaluated with a predesigned Microsoft Excel® Spreadsheet, and the kinetic parameters were fitted to a Michaelis-Menton model using the program Table Curve® from Jandel Scientific.

Results indicated that the $K_m$ for cGMP hydrolysis was 5 (±1) nM and the $K_m$ for cAMP hydrolysis was 160 (±30) μM. In the extract, cGMP hydrolytic activity was determined to be 0.035 (±0.01) μmol/min/mg, while cAMP hydrolysis was measured to be 0.52 (±0.06) μmol/min/mg. Thus, although PDE10 had much greater affinity for cGMP, the $V_{max}$ for cAMP was 15-fold greater.

In order to distinguish PDE10 from other PDE families, a panel of PDE inhibitors with activities against defined PDE families was tested for PDE10 inhibition using cAMP as a substrate. The results of the assay are set out in Table 1 below.

TABLE 1

PDE10 Inhibition with Isozyme-specific PDE Inhibitors

| Inhibitor | Target Family | PDE10 IC$_{50}$ ($\mu$M) | Target Family IC$_{50}$ ($\mu$M) |
|---|---|---|---|
| SCH46642 | PDE1 | 14 | 0.2[5] |
| EHNA | PDE2 | 477 | 0.8[2] |
| Cilostamide | PDE3 | 100 | 0.04–0.9[3] |
| Rolipram | PDE4 | 529 | 0.18–0.5[4] |
| DMPPO | PDE5 | 9 | 0.003[1] |
| IBMX | non-specific | 59 | 2–20[1] |

[1]Coste and Grodin, Biochem. Pharmacol. 50:1577–1585 (1995).
[2]Podzuweit, et al. Cell. Signaling 7:733–738 (1995)
[3]Manganiello et al., in IsoenzymesofCyclicNucleotidePhosphodiesterases, Beavo and Housley (Eds.), John Wiley and Sons, Ltd., pp. 87–116 (1990)
[4]Bolger et al., Mol. Cell. Biol. 13:6558–6571 (1993)
[5]Ahn, et al., Abstract from the 9th International Conference on Second Messengers and Phosphoproteins, Nashville, TN, 1995, p. 86.

The results further distinguish PDE10 from PDEs in families 1 through 5 in that specific inhibitors for enzymes in those families are significantly less effective in inhibiting PDE10.

EXAMPLE 5

Production of Anti-PDE10 Antibodies

A GST fusion protein was produced in *E. coli* to provide an antigen for generation of monoclonal antibodies to PDE10. An EcoRI fragment from FB76.2 (nucleotides 280 through 1829 in SEQ ID NO: 18) was inserted into the EcoRI site of pGEX3x (Pharmacia) and the resultant construct was transformed in the *E. coli* strain XL1 Blue. A GST-PDE10 fusion protein including 464 amino acids from PDE10 was expressed from this construct following induction with IPTG. The fusion protein was isolated using SDS-PAGE, the band of appropriate size excised from the gel following staining with cold 0.4 M KCl, and the protein obtained from the acrylamide by electroelution. The elution product was dialyzed against PBS and concentrated using Centriprep 10 and Centricon columns (Amicon, Beverly Mass.) prior to being injected into mice.

On day 0, four Balb/c mice were pre-bled and immunized by subcutaneous injection with a panel of antigens including 30 $\mu$g/mouse GST-PDE10 fusion protein in complete Freund's adjuvant in 200 $\mu$l total volume. The same injections were repeated at weeks three and nine in incomplete Freund's adjuvant. Ten days after the last immunization, test bleeds were obtained and screened by antigen capture ELISA and Western analysis.

In the ELISA, Immulon® 4 plates (Dynex, Cambridge, Mass.) were coated at 4° C. with 50 $\mu$l/well of a solution containing 2 $\mu$g/ml GST-PDE10 in 50 mM carbonate buffer, pH 9.6. Plates were blocked with 0.5% fish skin gelatin (Sigma) for 30 minutes and 50 $\mu$l serum diluted in PBS with 0.5% Tween® 20 (PBST) was added. Serum dilutions ranged from 1:100 to 1:102,400 and were obtained by a series of doubling dilutions. After incubation at 37° C. for 30 minutes and washing three times with PBST, 50 $\mu$l of horseradish peroxidase-conjugated goat anti-mouse IgG(fc) antibody (Jackson) (diluted 1:10000 in PBST) was added. Plates were incubated as above and washed four times with PBST. Antibody was detected with addition of tetramethyl benzidine (Sigma Chemical, St. Louis, Mo.) and the color reaction was stopped after five minutes with the addition of 50 $\mu$l of 15% $H_2SO_4$. Absorbance at 450 nM was measured on a plate reader.

For Western analysis, SDS-PAGE gels were run with approximately 10 $\mu$g yeast PDE10 extract and approximately 200 ng of gel-purified GST-PDE10 and the proteins were transferred to Immobilon-PVDF. A standard enhanced chemiluninescence (ECL) Western blot protocol was performed using BioRad goat anti-mouse IgG horseradish peroxidase as the secondary antibody.

In preparation of hybridomas, splenocytes from mice giving a positive result from the ELISA and/or Western blotting protocols above, were fused to NS-1 cells in a ratio of 5:1 by standard methods using polyethylene glycol 1500 (Boehringer Mannheim) [Harlow and Lane, Antibodies, a Laboratory Manual, Cold Spring Harbor Laboratory, p.211 (1988)]. The fused cells were resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×10$^6$ murine thymocytes/ml and dispensed into ten 96-well flat bottom tissue culture plates (Corning, United Kingdom) at 200 $\mu$l/well. Cells were fed on days 2, 4, and 6 post fusion by aspirating approximately 100 $\mu$l from each well with an 18 G needle (Becton Dickinson) and adding 100 $\mu$l/well plating medium described above except containing 10 units/ml IL-6 and lacking thymocytes. On days 9 to 12, supernatants from the fusion wells were screened by antigen capture ELISA using GST and GST-PDE10 and by ECL Western analysis as described above.

A positive signal of the expected size was obtained on both lanes of the Western blot using mouse blood and monoclonal antibodies with reactivity to the yeast recombinant protein were obtained in the subsequent fusion.

EXAMPLE 6

Analysis of PDE10 Expression by in situ Hybridization

Expression of PDE10 was examined in tissue sections by in situ hybridization as described below.
Preparation of Probe An EcoRI/PstI restriction enzyme fragment from the cDNA FB93a (corresponding to nucleotides 370 through 978 in SEQ ID NO: 22) was subcloned into a Bluescript® vector (Stratagene, La Jolla, Calif.) to generate an expression plasmid designated PDE10A3A. The plasmid was digested with EcoRI and transcribed with T3 polymerase to generate an antisense probe. A sense probe was generated by digestion the plasmid with BamHI and transcribing with T7 polymerase. The PDE10 templates were transcribed using a RNA Transcription kit (Stratagene, La Jolla, Calif.) in a reaction containing 5 $\mu$l of 5× transcription buffer (Stratagene), 30 mM DTT (Stratagene), 0.8 mM each ATP, CTP, GTP (10 mM (Stratagene), 40 U RNase Block II (Stratagene), 12.5 U T3 or T7 polymerase (Stratagene), and 300 ng linearized plasmid template, 50 $\mu$Ci $^{35}$S-UTP (greater than 1000 Ci/mmol, Amersham, Arlington Heights, Ill.). The mixture was incubated at 37° C. for one hour after which the template DNA was removed by addition of 1 $\mu$l of RNase-free DNase I (Stratagene) and incubation for 15 minutes at 37° C. The probe was hydrolyzed to approximately 250 nucleotides in length to facilitate tissue penetration by adding 4 $\mu$l 1 M NaHCO$_3$ and 6 $\mu$l 1 M Na$_2$CO$_3$ for 22 minutes at 60° C. and the reaction mixture was neutralized by addition of 25 $\mu$l of a solution containing 100 $\mu$l 3 M sodium acetate, 5 $\mu$l acetic acid (VWR, So. Plainfield, N.J.), and 395 µl dH$_2$O. A Quick Spin G50 RNA column (5'→3' Inc., Boulder, Co.) was prepared according to the manufacturer's suggested protocol. The probe was placed in the center of the column and the column centrifuged for four minutes at 1,000 rpm in a desk top centrifuge. The column flow-through was mixed with 50 µl dH$_2$O, 2 µl of a 10 mg/ml tRNA solution, 10 µl 3 M sodium acetate, and 200 µl 100% ethanol (VWR) and the resulting mixture was incubated at −20° C. overnight. The probe solution was microfuged for 15 minutes at 4° C., the supernatant was removed, and the pellet was resuspended in 40 µl 1× TBE containing 1 µl of 0.1 M DTT. The probe was stored at −70° C. until the in situ hybridization assay was performed.

Preparation of Tissue Samples and in situ Hybridization

Tissues (National Disease Research Interchange, Philadelphia, Pa. and Cooperative Human Tissue Network, Philadelphia, Pa.) were sectioned at 6 µm and placed on Superfrost Plus slides (VWR). Sections were fixed for 20 minutes at 4° C. in 4% paraformaldehyde (Sigma, St. Louis, Mo.). The slides were rinsed in three changes of 1× calcium-, magnesium-free phosphate buffered saline (CMF-PBS), dehydrated with three successive washes with 70% ethanol, 95% ethanol and 100% ethanol, and dried for 30 minutes at room temperature. The slides were placed in 70% formamide (J. T. Baker) in 2×SSC for two minutes at 70° C., rinsed in 2×SSC at 4° C., dehydrated through 70%, 95% and 100% ethanol washes, and dried for 30 minutes at room temperature.

A prehybridization step was performed by placing the slides in an airtight box containing a piece of filter paper saturated with buffer containing 50% formamide (J. T. Baker) in 4×SSC. Each section was covered with 100 µl of rHB2 buffer consisting of 10% dextran sulfate (Sigma), 50% formamide (J. T. Baker, Phillpsburg, N.J.), 100 mM DTT (Boehringer Mannheim, Indianapolis, Ind.), 0.3 M NaCl (Sigma), 20 mM Tris, pH 7.5, 5 mM EDTA (Sigma), and 1× Denhardt's solution (Sigma) and the slides were incubated at 42° C. for two hours. The probe, as described above, was prepared by mixing 4×10$^5$ cpm/tissue section with 5 µl of a 10 mg/ml tRNA solution per section and heating the mixture at 95° C. for three minutes. Ice cold rHB2 buffer was added to bring the final volume to 20 µl/section. The probe-containing solution (20 µl/section) was added to 100 µl rHB2 buffer previously applied. The slides were incubated at 55° C. for 12 to 16 hours. Following hybridization, the slides were washed once in 4×SSC containing 10 mM DTT for one hour at room temperature, once in 50% deionized formamide (J. T. Baker), 1×SSC, and 1 mM DTT for 40 minutes at 60° C., once in 2×SSC for 30 minutes at room temperature, and once in 0.1×SSC for 30 minutes at room temperature. The sections were dehydrated through 70%, 95%, and 100% ethanol washes and air dried for 30 minutes. The slides were dipped in Kodak NTB2 nuclear emulsion, dried for one to three hours at room temperature in the dark, and stored in the dark at 4° C. with desiccant until time of development. The slides were developed in 4° C. Kodak Dektol® developer for two minutes, dipped four times in 4° C. dH$_2$O, and placed in 4° C. Kodak fixer for ten minutes. The slides were rinsed in dH$_2$O and a standard hematoxylin and eosin (H&E) stain was performed as follows.

The slides were rinsed in dH$_2$O and stained with hematoxylin and eosin by transfer of the slides through a series of the following steps: five minutes in formaldehyde/alcohol (100 ml formaldehyde, 900 ml 80% ethanol); three rinses in water for a total of two minutes; five minutes in 0.75% Harris hematoxylin (Sigma); three rinses in water for a total of two minutes; one dip in 1% HCl/50% ethanol; one rinse in water; four dips in 1% lithium carbonate; ten minutes in tap water; two minutes in 0.5% eosin (Sigma); three rinses in water for a total of two minutes; two minutes in 70% ethanol; three one-minute rinses in 95% ethanol; two one-minute rinses in 100% ethanol; and two two-minute rinses in xylene. Slides were mounted with cytoseal 60 (Stephens Scientific, Riverdale, N.J.).

The signals obtained with an antisense PDE10 probe were compared to the control signals generated by a sense PDE10 probe and any signal specific to the antisense probe was assumed to represent PDE10 expression. PDE10 signal was detected throughout much of the cerebellum, with very strong signal in the Purkinje cells.

EXAMPLE 7

High Throughput Screening for PDE10 Inhibitors

In an attempt to identify specific inhibitors, PDE10 was screened against a chemical library containing compounds of known structure. Initial screening was performed on pools of compounds (22 compounds per pool) with each compound present at 4.6 µM. Pools which inhibited PDE10 activity by greater than 50% were selected and the individual compounds in the pool were screened at a concentration of 20 µM. IC$_{50}$ values were determined for compounds that inhibited enzyme activity.

An extract was prepared from *Saccharomyces cerevisiae* strain BJ2-54 (described in Example 4) lacking endogenous PDE activity and having PDE10 at an activity of 49 nmol cGMP hydrolyzed/min/mg with 32 nM cGMP. The extract was diluted 1:21,000-fold for use in the assay. Dilution buffer included 25 mM Tris, pH 8.0, 0.1 mM DTT, 5.0 mM MgCl$_2$, 100 mM NaCl, 5 µM ZnSO$_4$ and 100 µg/ml BSA. PDE assay buffer (5×) contained 200 mM Tris, pH 8.0, 5 mM EGTA, 25 mM MgCl$_2$ and 0.5 mg/ml BSA. Just prior to screening, 5×PDE assay buffer, deionized water, and 5'-nucleosidase (stock solution 15 mg/ml snake venom 5'-nucleosidase in 20 mM Tris, pH 8.0) were mixed at ratios of 4:4:1 to make Assay Reagent Mix.

A Packard MultiPROBE® was used to add 45 µl of the Assay Reagent Mix and 20 µl of the chemical compound pools. A BIOMEK® 1000 (See Example 4) was used to add 20 µl of PDE10 extract diluted as described above and 20 µl $^{32}$P-cGMP (ICN, specific activity 250 µCi/mmol, diluted to 0.4 µCi/ml, 16 nM, in deionized water). Final cGMP concentration in the assay was 0.08 µCi/ml, 3.2 nM. Ten minutes after addition of $^{32}$P-cGMP, 140 µl of 25 mg/ml charcoal (in 0.1 M NaH$_2$PO$_4$) was added to stop the reaction. After a 20 minute incubation at room temperature, the assay plates were centrifuged for five minutes at 3,500 rpm in a Beckman GS-6R centrifuge. A BIOMEK® 1000 was used to transfer 140 µl of the supernatant to a Wallac counting plate and Cerenkov radiation was measured in a Wallac Micro-Beta Counter.

Several compounds that merit further investigation were found to inhibit enzyme activity.

Numerous modifications and variations in the invention as set forth in the above illustrative examples are expected to occur to those skilled in the art. Consequently only such limitations as appear in the appended claims should be placed on the invention.

What is claimed is:

1. A polynucleotide encoding a polypeptide comprising an amino acid sequence selected from the group consisting of SEQ ID NO: 2, SEQ ID NO: 19. SEQ ID NO: 21 and SFQ ID NO: 23.

2. The polynucleotide according to claim 1 comprising the sequence set forth in SEQ ID NO: 1.

3. A polynucleotide encoding a human phosphodiesterase 10 (PDE10) polypeptide with PDE10 enzymatic activity selected from the group consisting of:

a) the polynucleotide according to claim 2;
   b) a polynucleotide encoding a polypeptide comprising an amino acid sequence selected from the group consisting of SEQ ID NO: 2, SEQ ID NO: 19, SEQ ID NO: 21 and SEQ ID NO: 23, and
   c) a DNA which hybridizes under moderately stringent conditions to the non-coding strand of the polynucleotide of (a) or (b); said moderately stringent conditions comprising a final wash at 65° C. in 2×SSC and 0.1% SDS.

4. The polynucleotide of claim 3 comprising the polynucleotide sequence set out in SEQ ID NO: 18.

5. The polynucleotide of claim 3 comprising the polynucleotide sequence set out in SEQ ID NO: 20.

6. The polynucleotide of claim 3 comprising the polynucleotide sequence set out in SEQ ID NO: 22.

7. The polynucleotide of claim 3 which is a DNA molecule.

8. The DNA of claim 7 which is a cDNA molecule.

9. The DNA of claim 7 which is a wholly or partially chemically synthesized DNA molecule.

10. A expression construct comprising the polynucleotide according to claim 3.

11. A host cell transformed or transfected with the expression construct according to claim 10.

12. A method for producing a PDE10 polypeptide comprising the steps of:

a) growing the host cell according to claim 11 under conditions appropriate for expression of the PDE10 polypeptide and
   b) isolating the PDE10 polypeptide from the host cell or the medium of its growth.

* * * * *

UNITED STATES PATENT AND TRADEMARK OFFICE
CERTIFICATE OF CORRECTION

PATENT NO.    : 6,350,603 B1                                          Page 1 of 1
DATED         : February 26, 2002
INVENTOR(S)   : Kate Loughney It is certified that error appears in the above-identified patent and that said Letters Patent is hereby corrected as shown below:

Column 3,
Lines 1-2, "SEQ 1D NO19, SEQ 1D NO: 21 and SEQ 1D NO 23" should be
-- SEQ 1D NO: 2, SEQ 1D NO: 18, SEQ 1D NO: 20 and SEQ 1D NO: 22 --.
Line 16, "thereof" should be -- thereof. --.

Column 11,
Line 57, "MRNA" should be -- mRNA --.

Column 12,
Line 42, "6679, pp. 25-20" should be -- 6679, p. 25 --.

Column 13,
Line 8, "intramarnmary" should be -- intramammary --.

Column 14,
Line 41, "D4" should be -- 4D --.

Column 17,
Lines 41 and 49, "A1 58300" should be -- A158300 --.

Column 19,
Line 8, "PDE10 A" should be -- PDE10A --.

Signed and Sealed this

Nineteenth Day of November, 2002

Attest:

JAMES E. ROGAN
Attesting Officer                    Director of the United States Patent and Trademark Office

SEQUENCE LISTING

<160> NUMBER OF SEQ ID NOS: 26

<210> SEQ ID NO 1
<211> LENGTH: 1548
<212> TYPE: DNA
<213> ORGANISM: Homo sapiens
<220> FEATURE:
<221> NAME/KEY: CDS
<222> LOCATION: (26)..(1423)

<400> SEQUENCE: 1

```
cccaaggcca tctacctgga catcg atg gac gca ttc aga agc act ccg tac        52
                            Met Asp Ala Phe Arg Ser Thr Pro Tyr
                             1               5 aaa gtg aga cct gtg gcc atc aag caa ctc tcc gag aga gaa gaa tta       100
Lys Val Arg Pro Val Ala Ile Lys Gln Leu Ser Glu Arg Glu Glu Leu
 10              15                  20                  25 atc cag agc gtg ctg gcg cag gtt gca gag cag ttc tca aga gca ttc       148
Ile Gln Ser Val Leu Ala Gln Val Ala Glu Gln Phe Ser Arg Ala Phe
             30                  35                  40 aaa atc aat gaa ctg aaa gct gaa gtt gca aat cac ttg gct gtc cta       196
Lys Ile Asn Glu Leu Lys Ala Glu Val Ala Asn His Leu Ala Val Leu
         45                  50                  55 gag aaa cgc gtg gaa ttg gaa gga cta aaa gtg gtg gag att gag aaa       244
Glu Lys Arg Val Glu Leu Glu Gly Leu Lys Val Val Glu Ile Glu Lys
     60                  65                  70 tgc aag agt gac att aag aag atg agg gag gag ctg gcg gcc aga agc       292
Cys Lys Ser Asp Ile Lys Lys Met Arg Glu Glu Leu Ala Ala Arg Ser
 75                  80                  85 agc agg acc aac tgc ccc tgt aag tac agt ttt ttg gat aac cac aag       340
Ser Arg Thr Asn Cys Pro Cys Lys Tyr Ser Phe Leu Asp Asn His Lys
 90                  95                 100                 105 aag ttg act cct cga cgc gat gtt ccc act tac ccc aag tac ctg ctc       388
Lys Leu Thr Pro Arg Arg Asp Val Pro Thr Tyr Pro Lys Tyr Leu Leu
             110                 115                 120 tct cca gag acc atc gag gcc ctg cgg aag ccg acc ttt gac gtc tgg       436
Ser Pro Glu Thr Ile Glu Ala Leu Arg Lys Pro Thr Phe Asp Val Trp
             125                 130                 135 ctt tgg gag ccc aat gag atg ctg agc tgc ctg gag cac atg tac cac       484
Leu Trp Glu Pro Asn Glu Met Leu Ser Cys Leu Glu His Met Tyr His
         140                 145                 150 gac ctc ggg ctg gtc agg gac ttc agc atc aac cct gtc acc ctc agg       532
Asp Leu Gly Leu Val Arg Asp Phe Ser Ile Asn Pro Val Thr Leu Arg
 155                 160                 165 agg tgg ctg ttc tgc gtc cac gac aac tac aga aac aac ccc ttc cac       580
Arg Trp Leu Phe Cys Val His Asp Asn Tyr Arg Asn Asn Pro Phe His
170                 175                 180                 185 aac ttc cgg cac tgc ttc tgc gtg gcc cag atg atg tac agc atg gtc       628
Asn Phe Arg His Cys Phe Cys Val Ala Gln Met Met Tyr Ser Met Val
             190                 195                 200 tgg ctc tgc agt ctc cag gag aag ttc tca caa acg gat atc ctg atc       676
Trp Leu Cys Ser Leu Gln Glu Lys Phe Ser Gln Thr Asp Ile Leu Ile
         205                 210                 215 cta atg aca gcg gcc atc tgc cac gat ctg gac cat ccc ggc tac aac       724
Leu Met Thr Ala Ala Ile Cys His Asp Leu Asp His Pro Gly Tyr Asn
     220                 225                 230 aac acg tac cag atc aat gcc cgc aca gag ctg gcg gtc cgc tac aat       772
Asn Thr Tyr Gln Ile Asn Ala Arg Thr Glu Leu Ala Val Arg Tyr Asn
 235                 240                 245
```

```
gac atc tca ccg ctg gag aac cac cac tgc gcc gtg gcc ttc cag atc      820
Asp Ile Ser Pro Leu Glu Asn His His Cys Ala Val Ala Phe Gln Ile
250                 255                 260                 265 ctc gcc gag cct gag tgc aac atc ttc tcc aac atc cca cct gat ggg      868
Leu Ala Glu Pro Glu Cys Asn Ile Phe Ser Asn Ile Pro Pro Asp Gly
                270                 275                 280 ttc aag cag atc cga cag gga atg atc aca tta atc ttg gcc act gac      916
Phe Lys Gln Ile Arg Gln Gly Met Ile Thr Leu Ile Leu Ala Thr Asp
            285                 290                 295 atg gca aga cat gca gaa att atg gat tct ttc aaa gag aaa atg gag      964
Met Ala Arg His Ala Glu Ile Met Asp Ser Phe Lys Glu Lys Met Glu
        300                 305                 310 aat ttt gac tac agc aac gag gag cac atg acc ctg ctg aag atg att     1012
Asn Phe Asp Tyr Ser Asn Glu Glu His Met Thr Leu Leu Lys Met Ile
    315                 320                 325 ttg ata aaa tgc tgt gat atc tct aac gag gtc cgt cca atg gaa gtc     1060
Leu Ile Lys Cys Cys Asp Ile Ser Asn Glu Val Arg Pro Met Glu Val
330                 335                 340                 345 gca gag cct tgg gtg gac tgt tta tta gag gaa tat ttt atg cag agc     1108
Ala Glu Pro Trp Val Asp Cys Leu Leu Glu Glu Tyr Phe Met Gln Ser
                350                 355                 360 gac cgt gag aag tca gaa ggc ctt cct gtg gca ccg ttc atg gac cga     1156
Asp Arg Glu Lys Ser Glu Gly Leu Pro Val Ala Pro Phe Met Asp Arg
            365                 370                 375 gac aaa gtg acc aag gcc aca gcc cag att ggg ttc atc aag ttt gtc     1204
Asp Lys Val Thr Lys Ala Thr Ala Gln Ile Gly Phe Ile Lys Phe Val
        380                 385                 390 ctg atc cca atg ttt gaa aca gtg acc aag ctc ttc ccc atg gtt gag     1252
Leu Ile Pro Met Phe Glu Thr Val Thr Lys Leu Phe Pro Met Val Glu
    395                 400                 405 gag atc atg ctg cag cca ctt tgg gaa tcc cga gat cgc tac gag gag     1300
Glu Ile Met Leu Gln Pro Leu Trp Glu Ser Arg Asp Arg Tyr Glu Glu
410                 415                 420                 425 ctg aag cgg ata gat gac gcc atg aaa gag tta cag aag aag act gac     1348
Leu Lys Arg Ile Asp Asp Ala Met Lys Glu Leu Gln Lys Lys Thr Asp
                430                 435                 440 agc ttg acg tct ggg gcc acc gag aag tcc aga ggg aga agc aga gat     1396
Ser Leu Thr Ser Gly Ala Thr Glu Lys Ser Arg Gly Arg Ser Arg Asp
            445                 450                 455 gtg aaa aac agt gaa gga gac tgt gcc tgaggaaagc gggggcgtg            1443
Val Lys Asn Ser Glu Gly Asp Cys Ala
        460                 465 gctgcagttc tggacgggct ggccgagctg cgcgggatcc ttgtgcaggg aagagctgcc   1503
ctgggcacct ggcaccacaa gaccatgttt tctaagaacc atttt                   1548

<210> SEQ ID NO 2
<211> LENGTH: 466
<212> TYPE: PRT
<213> ORGANISM: Homo sapiens

<400> SEQUENCE: 2

Met Asp Ala Phe Arg Ser Thr Pro Tyr Lys Val Arg Pro Val Ala Ile
1               5                   10                  15

Lys Gln Leu Ser Glu Arg Glu Glu Leu Ile Gln Ser Val Leu Ala Gln
            20                  25                  30

Val Ala Glu Gln Phe Ser Arg Ala Phe Lys Ile Asn Glu Leu Lys Ala
        35                  40                  45

Glu Val Ala Asn His Leu Ala Val Leu Glu Lys Arg Val Glu Leu Glu
    50                  55                  60
```

```
Gly Leu Lys Val Val Glu Ile Glu Lys Cys Lys Ser Asp Ile Lys Lys
 65                  70                  75                  80

Met Arg Glu Glu Leu Ala Ala Arg Ser Ser Arg Thr Asn Cys Pro Cys
                 85                  90                  95

Lys Tyr Ser Phe Leu Asp Asn His Lys Lys Leu Thr Pro Arg Arg Asp
            100                 105                 110

Val Pro Thr Tyr Pro Lys Tyr Leu Leu Ser Pro Glu Thr Ile Glu Ala
        115                 120                 125

Leu Arg Lys Pro Thr Phe Asp Val Trp Leu Trp Glu Pro Asn Glu Met
    130                 135                 140

Leu Ser Cys Leu Glu His Met Tyr His Asp Leu Gly Leu Val Arg Asp
145                 150                 155                 160

Phe Ser Ile Asn Pro Val Thr Leu Arg Arg Trp Leu Phe Cys Val His
                165                 170                 175

Asp Asn Tyr Arg Asn Asn Pro Phe His Asn Phe Arg His Cys Phe Cys
            180                 185                 190

Val Ala Gln Met Met Tyr Ser Met Val Trp Leu Cys Ser Leu Gln Glu
        195                 200                 205

Lys Phe Ser Gln Thr Asp Ile Leu Ile Leu Met Thr Ala Ala Ile Cys
    210                 215                 220

His Asp Leu Asp His Pro Gly Tyr Asn Asn Thr Tyr Gln Ile Asn Ala
225                 230                 235                 240

Arg Thr Glu Leu Ala Val Arg Tyr Asn Asp Ile Ser Pro Leu Glu Asn
                245                 250                 255

His His Cys Ala Val Ala Phe Gln Ile Leu Ala Glu Pro Glu Cys Asn
            260                 265                 270

Ile Phe Ser Asn Ile Pro Pro Asp Gly Phe Lys Gln Ile Arg Gln Gly
        275                 280                 285

Met Ile Thr Leu Ile Leu Ala Thr Asp Met Ala Arg His Ala Glu Ile
    290                 295                 300

Met Asp Ser Phe Lys Glu Lys Met Glu Asn Phe Asp Tyr Ser Asn Glu
305                 310                 315                 320

Glu His Met Thr Leu Leu Lys Met Ile Leu Ile Lys Cys Cys Asp Ile
                325                 330                 335

Ser Asn Glu Val Arg Pro Met Glu Val Ala Glu Pro Trp Val Asp Cys
            340                 345                 350

Leu Leu Glu Glu Tyr Phe Met Gln Ser Asp Arg Glu Lys Ser Glu Gly
        355                 360                 365

Leu Pro Val Ala Pro Phe Met Asp Arg Asp Lys Val Thr Lys Ala Thr
    370                 375                 380

Ala Gln Ile Gly Phe Ile Lys Phe Val Leu Ile Pro Met Phe Glu Thr
385                 390                 395                 400

Val Thr Lys Leu Phe Pro Met Val Glu Glu Ile Met Leu Gln Pro Leu
                405                 410                 415

Trp Glu Ser Arg Asp Arg Tyr Glu Glu Leu Lys Arg Ile Asp Asp Ala
            420                 425                 430

Met Lys Glu Leu Gln Lys Lys Thr Asp Ser Leu Thr Ser Gly Ala Thr
        435                 440                 445

Glu Lys Ser Arg Gly Arg Ser Arg Asp Val Lys Asn Ser Glu Gly Asp
    450                 455                 460

Cys Ala
465
```

```
<210> SEQ ID NO 3
<211> LENGTH: 225
<212> TYPE: DNA
<213> ORGANISM: Homo sapiens
<220> FEATURE:
<223> OTHER INFORMATION: Nucleotides at positions 130, 186, and 205 are
      either A, T, G, or C.

<400> SEQUENCE: 3
agcgaccgtg agaagtcaga aggccttcct gtggaaccgt tcatggaccg agacaaagtg      60
accaaggcca cagcccagat tgggttcatc aagtttgccc tgatcccaat gtttgaaaca     120
gtgaccaagn tcttccccat ggttgaggag atcatgctgc agccactttg ggaatcccga     180
gatcgntacg aggagctgaa gcggntagat gacgccatga aagag                     225

<210> SEQ ID NO 4
<211> LENGTH: 158
<212> TYPE: DNA
<213> ORGANISM: Homo sapiens
<220> FEATURE:
<223> OTHER INFORMATION: Nucleotides at positions 12, 36, 61, and 109
      are either A, T, G, or C.

<400> SEQUENCE: 4
gtaccagatc antgcccgca cagagctggc ggtccgntac aatgacatct caccgttgga      60
gnaaccacca ctgcgccgtg gccttccaga tcctcgccga gcctgagtgn aacatcttct     120
ccaacatccc acctgatggg ttcaagcaga tccgacag                             158

<210> SEQ ID NO 5
<211> LENGTH: 98
<212> TYPE: DNA
<213> ORGANISM: Homo sapiens
<220> FEATURE:
<223> OTHER INFORMATION: Nucleotides at positions 14, 22, and 50 are
      either A, T, C, or G.

<400> SEQUENCE: 5
gagaacacca ctgngccgtg gncttccaga tcctcgccga gcctgagtgn aacatcttct      60
ccaacatccc acctgatggg ttcaagcaga tccgacag                              98

<210> SEQ ID NO 6
<211> LENGTH: 418
<212> TYPE: DNA
<213> ORGANISM: Homo sapiens
<220> FEATURE:
<223> OTHER INFORMATION: Nucleotides at positions 1, 267, 352, 400, and
      411 are either A, T, G, or C.

<400> SEQUENCE: 6
nggttaactg gcgcatcttg tctttctctg agaacagcga tctggttatg gggcatttct      60
gtctctaatg tcactgtctg ctgcattccc tgcagagcga ccgtgagaag tcagaaggcc     120
ttcccgtggc cccgttcatg gaccgagaca agtgaccaa ggccacagcc caggattggg     180
tttcatcaag tttgtcctga tcccaatgtt tgaaacagtg accaagctct ccccatggg     240 ttgagggaga ttcatgctgg cagccanttt ggggaatccc gaggattcgc tacgagggag     300
cttgaagcgg gattaggatg gacggccatg gaaaggagtt ttacaggaag gnaggatttg     360
acagttttga agttttgggg gggccaccga ggaagttccn ggaggaggag naggcaga       418

<210> SEQ ID NO 7
<211> LENGTH: 428
<212> TYPE: DNA
```

<210> SEQ ID NO 7
<211> LENGTH: 428
<212> TYPE: DNA
<213> ORGANISM: Homo sapiens
<220> FEATURE:
<223> OTHER INFORMATION: Nucleotides at positions 1, 82, 92, 130, 347, 390, and 396 are either A, T, G, or C.

<400> SEQUENCE: 7

```
nagaaaaaag tgaacaaaat ggttcttaga aaacatggtc ttgtggtgcc aggtgcccag      60
ggagctcttc cctgcacaag gntcccgcgc antcggccag cccgtccaga actgcagcca     120
cgcccccgn tttcctcagg cacagtctcc ttcactgttt ttcacatctc tgcttctctc     180
tctggacttc tcggtgggcc cagacgtcaa gctgtcagtc ttcttctgta actctttcat     240
gggcgtcatc tatccgcttc agctcctcgt aggcgatctc ggggattccc aaagtgggct     300
gcagcatgat cttcctcaac catggggggg aggagcttgg ggcactngtt ttcaaaaatt     360
gggggatcag gggacaaact tgattggan cccatnttgg ggcttttggg cctttggggc     420
aattttttg                                                             428
```

<210> SEQ ID NO 8
<211> LENGTH: 438
<212> TYPE: DNA
<213> ORGANISM: Homo sapiens
<220> FEATURE:
<223> OTHER INFORMATION: Nucleotides at positions 63, 98, 107, 188, 203, 206, 238, 252, 297, 370, 389, and 427 are either A, T, G, or C.

<400> SEQUENCE: 8

```
tttttttttt tttttttttgt atcagtgaac aaaatggttc ttagaaaaca tggtcttgtg      60
gtnccaggtg cccagggagc tcttccctgc acaaggancc cgcgcantcg gccagcccgt     120
ccagaactgc agccacgccc ccgtttttcc tcaggcacag tctccttcac tgttttttcac     180
atctctgntt ctctctctgg ganttntcgg tgggccccag aacgtcaagc tgtcagtntt     240
cttctgtaac tntttcatgg gcgtcatcta tccgtttcag cttcctcgta ggcgatnttg     300
gggattccca aagtgggctg cagcatggga tcttcctcaa accatggggg gaaggagttt     360
gggtcaattn ttttcaaaac attgggggnt cagggacaaa attttgatgg aaacccaatt     420
tgggggntgt gggccttg                                                   438
```

<210> SEQ ID NO 9
<211> LENGTH: 262
<212> TYPE: DNA
<213> ORGANISM: Mus musculus

<400> SEQUENCE: 9

```
gagaattttg actacagcaa cgaggagcac ctgaccctgc tgaagatgat tctcataaaa      60
tgctgtgata tctccaatga agtccgtccc atggaggtgg cagaatcgtg ggtggactgt     120
ttactggaag aatattttat gcagagtgac cgtgagaagt ccgaagcctt cctgtggccc     180
cattcatgga ccgagacaaa gtgaccaaag caacagccca aattgggttc atcaagtttg     240
tcctgatccc aatgtttgaa ac                                              262
```

<210> SEQ ID NO 10
<211> LENGTH: 250
<212> TYPE: DNA
<213> ORGANISM: Mus musculus

<400> SEQUENCE: 10

```
gagaattttg actacagcaa cgaggagcac ctgaccctgc tgaagatgat tctcataaaa      60
```

-continued

| | |
|---|---|
| tgctgtgata tctccaatga agtccgtccc atggaggtgg cagaatcgtg ggtggactgt | 120 |
| ttactggaag aatattttat gcagagtgac cgtgagaagt ccgaagcctt cctgtggccc | 180 |
| attcatggac cgagacaaag tgaccaaagc aacagccaaa ttgggttcat caagtttgtc | 240 |
| tgtccaatgt | 250 |

<210> SEQ ID NO 11
<211> LENGTH: 459
<212> TYPE: DNA
<213> ORGANISM: Homo sapiens
<220> FEATURE:
<223> OTHER INFORMATION: Nucleotides at positions 155, 393, and 442 are
either A, T, G, or C.

<400> SEQUENCE: 11

| | |
|---|---|
| attaatcttg gccactgaca tggcaagaca tgcagaaatt atggattctt tcaaagagaa | 60 |
| aatgagagaat tttgactaca gcaacgagga gcacatgacc ctggtgagtg gcttattctg | 120 |
| cctgggtggg cagccaggcg gttgggctgg cgaanaggtt catccatcca gctcacactg | 180 |
| gaagccaaga agctgaaatt attagtcttc ttggaacaag gtgtctataa atctggttt | 240 |
| caaggtcatg actcttacta ggaaagtccg ggcagggcct ccctcctgat gggtcctcct | 300 |
| tcatggtcag aggcagcatt ctcccattcc tccatctctt ttgggatttt gaaggagata | 360 |
| aagtggggtg aaggccgtgc attctcgctc tgnttttcca gagaattaaa accagttttc | 420 |
| ccttgaaggc acagccccag cntggcattt tgaaagttg | 459 |

<210> SEQ ID NO 12
<211> LENGTH: 599
<212> TYPE: DNA
<213> ORGANISM: Homo sapiens
<220> FEATURE:
<221> NAME/KEY: CDS
<222> LOCATION: (99)..(443)

<400> SEQUENCE: 12

| | |
|---|---|
| tggccctcga ggccaagaat tcggcacgag tggttaactg gcgcatcttg tctttctctg | 60 |
| agaacagcga tctggttatg gggcatttct gtctctaa tgt cac tgt ctg ctg cat | 116 |
|                                                                          Cys His Cys Leu Leu His | |
|                                                                            1              5 | |
| tcc ctg cag agc gac cgt gag aag tca gaa ggc ctt ccc gtg gcc ccg | 164 |
| Ser Leu Gln Ser Asp Arg Glu Lys Ser Glu Gly Leu Pro Val Ala Pro | |
|           10                  15                  20 | |
| ttc atg gac cga gac aaa gtg acc aag gcc aca gcc cag att ggg ttc | 212 |
| Phe Met Asp Arg Asp Lys Val Thr Lys Ala Thr Ala Gln Ile Gly Phe | |
|         25                  30                  35 | |
| atc aag ttt gtc ctg atc cca atg ttt gaa aca gtg acc aag ctc ttc | 260 |
| Ile Lys Phe Val Leu Ile Pro Met Phe Glu Thr Val Thr Lys Leu Phe | |
| 40                  45                  50 | |
| ccc atg gtt gag gag atc atg ctg cag cca ctt tgg gaa tcc cga gat | 308 |
| Pro Met Val Glu Glu Ile Met Leu Gln Pro Leu Trp Glu Ser Arg Asp | |
| 55                  60                  65                  70 | |
| cgc tac gag gag ctg aag cgg ata gat gac gcc atg aaa gag tta cag | 356 |
| Arg Tyr Glu Glu Leu Lys Arg Ile Asp Asp Ala Met Lys Glu Leu Gln | |
|                 75                  80                  85 | |
| aag aag act gac agc ttg acg tct ggg gcc acc gag aag tcc aga gag | 404 |
| Lys Lys Thr Asp Ser Leu Thr Ser Gly Ala Thr Glu Lys Ser Arg Glu | |
|               90                  95                100 | |
| aga agc aga gat gtg aaa aac agt gaa gga gac tgt gcc tgaggaaagc | 453 |
| Arg Ser Arg Asp Val Lys Asn Ser Glu Gly Asp Cys Ala | |
|         105                  110                  115 | |

```
gggggggcgtg gctgcagttc tggacgggct ggccgagctg cgcgggatcc ttgtgcaggg    513
aagagctgcc ctgggcacct ggcaccacaa gaccatgttt tctaagaacc attttgttca    573
ctgatacaaa aaaaaaaaaa aaaaaa                                          599
```

<210> SEQ ID NO 13
<211> LENGTH: 115
<212> TYPE: PRT
<213> ORGANISM: Homo sapiens

<400> SEQUENCE: 13

```
Cys His Cys Leu Leu His Ser Leu Gln Ser Asp Arg Glu Lys Ser Glu
  1               5                  10                  15

Gly Leu Pro Val Ala Pro Phe Met Asp Arg Asp Lys Val Thr Lys Ala
             20                  25                  30

Thr Ala Gln Ile Gly Phe Ile Lys Phe Val Leu Ile Pro Met Phe Glu
         35                  40                  45

Thr Val Thr Lys Leu Phe Pro Met Val Glu Glu Ile Met Leu Gln Pro
     50                  55                  60

Leu Trp Glu Ser Arg Asp Arg Tyr Glu Glu Leu Lys Arg Ile Asp Asp
 65                  70                  75                  80

Ala Met Lys Glu Leu Gln Lys Lys Thr Asp Ser Leu Thr Ser Gly Ala
                 85                  90                  95

Thr Glu Lys Ser Arg Glu Arg Ser Arg Asp Val Lys Asn Ser Glu Gly
            100                 105                 110

Asp Cys Ala
        115
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 14

```
agtcgaattc accgtgagaa gtcagaag                                        28
```

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 15

```
gtcaaagctt acatggtctt gtggtgcc                                        28
```

<210> SEQ ID NO 16
<211> LENGTH: 1303
<212> TYPE: DNA
<213> ORGANISM: Homo sapiens
<220> FEATURE:
<221> NAME/KEY: CDS
<222> LOCATION: (107)..(1066)

<400> SEQUENCE: 16

```
agtgactcta ctttgtgaaa atgtgaaact tcgtgtaggt actcagtaaa tcagtaaatt     60
cttactaacg ttagccccca gcctagctat ggagggtgca tgctga gcc ctg gag      115
                                                     Ala Leu Glu
                                                      1
```

```
cac atg tac cac gac ctc ggg ctg gtc agg gac ttc agc atc aac cct      163
His Met Tyr His Asp Leu Gly Leu Val Arg Asp Phe Ser Ile Asn Pro
     5                  10                  15 gtc acc ctc agg agg tgg ctg ttc tgc gtc cac gac aac tac aga aac      211
Val Thr Leu Arg Arg Trp Leu Phe Cys Val His Asp Asn Tyr Arg Asn
 20              25                  30                  35 aac ccc ttc cac aac ttc cgg cac tgc ttc tgc gtg gcc cag atg atg      259
Asn Pro Phe His Asn Phe Arg His Cys Phe Cys Val Ala Gln Met Met
                 40                  45                  50 tac agc atg gtc tgg ctc tgc agt ctc cag gag aag ttc tca caa acg      307
Tyr Ser Met Val Trp Leu Cys Ser Leu Gln Glu Lys Phe Ser Gln Thr
             55                  60                  65 gat atc ctg atc cta atg aca gcg gcc atc tgc cac gat ctg gac cat      355
Asp Ile Leu Ile Leu Met Thr Ala Ala Ile Cys His Asp Leu Asp His
         70                  75                  80 ccc ggc tac aac aac acg tac cag atc aat gcc cgc aca gag ctg gcg      403
Pro Gly Tyr Asn Asn Thr Tyr Gln Ile Asn Ala Arg Thr Glu Leu Ala
 85                  90                  95 gtc cgc tac aat gac atc tca ccg ctg gag aac cac cac tgc gcc gtg      451
Val Arg Tyr Asn Asp Ile Ser Pro Leu Glu Asn His His Cys Ala Val
100             105                 110                 115 gcc ttc cag atc ctc gcc gag cct gag tgc aac atc ttc tcc aac atc      499
Ala Phe Gln Ile Leu Ala Glu Pro Glu Cys Asn Ile Phe Ser Asn Ile
                120                 125                 130 cca cct gat ggg ttc aag cag atc cga cag gga atg atc aca tta atc      547
Pro Pro Asp Gly Phe Lys Gln Ile Arg Gln Gly Met Ile Thr Leu Ile
            135                 140                 145 ttg gcc act gac atg gca aga cat gca gaa att atg gat tct ttc aaa      595
Leu Ala Thr Asp Met Ala Arg His Ala Glu Ile Met Asp Ser Phe Lys
        150                 155                 160 gag aaa atg gag aat ttt gac tac agc aac gag gag cac atg acc ctg      643
Glu Lys Met Glu Asn Phe Asp Tyr Ser Asn Glu Glu His Met Thr Leu
    165                 170                 175 ctg aag atg att ttg ata aaa tgc tgt gat atc tct aac gag gtc cgt      691
Leu Lys Met Ile Leu Ile Lys Cys Cys Asp Ile Ser Asn Glu Val Arg
180                 185                 190                 195 cca atg gaa gtc gca gag cct tgg gtg gac tgt tta tta gag gaa tat      739
Pro Met Glu Val Ala Glu Pro Trp Val Asp Cys Leu Leu Glu Glu Tyr
                200                 205                 210 ttt atg cag agc gac cgt gag aag tca gaa ggc ctt cct gtg gca ccg      787
Phe Met Gln Ser Asp Arg Glu Lys Ser Glu Gly Leu Pro Val Ala Pro
            215                 220                 225 ttc atg gac cga gac aaa gtg acc aag gcc aca gcc cag att ggg ttc      835
Phe Met Asp Arg Asp Lys Val Thr Lys Ala Thr Ala Gln Ile Gly Phe
        230                 235                 240 atc aag ttt gtc ctg atc cca atg ttt gaa aca gtg acc aag ctc ttc      883
Ile Lys Phe Val Leu Ile Pro Met Phe Glu Thr Val Thr Lys Leu Phe
    245                 250                 255 ccc atg gtt gag gag atc atg ctg cag cca ctt tgg gaa tcc cga gat      931
Pro Met Val Glu Glu Ile Met Leu Gln Pro Leu Trp Glu Ser Arg Asp
260                 265                 270                 275 cgc tac gag gag ctg aag cgg ata gat gac gcc atg aaa gag tta cag      979
Arg Tyr Glu Glu Leu Lys Arg Ile Asp Asp Ala Met Lys Glu Leu Gln
                280                 285                 290 aag aag act gac agc ttg acg tct ggg gcc acc gag aag tcc aga gag     1027
Lys Lys Thr Asp Ser Leu Thr Ser Gly Ala Thr Glu Lys Ser Arg Glu
            295                 300                 305 aga agc aga gat gtg aaa aac agt gaa gga gac tgt gcc tgaggaaagc      1076
Arg Ser Arg Asp Val Lys Asn Ser Glu Gly Asp Cys Ala
        310                 315                 320
```

-continued

```
gggggcgtg gctgcagttc tggacgggct ggccgagctg cgcgggatcc ttgtgcaggg      1136
aagagctgcc ctgggcacct ggcaccacaa gaccatgttt tctaagaacc attttgttca      1196
ctgatacaaa aaaaaaaaag gaattcatga tgctgtacag aattttattt ttaaactgtc      1256
ttttaaataa tatattctta tacggaaaaa aaaaaaaaaa aaaaaaa                    1303
```

<210> SEQ ID NO 17
<211> LENGTH: 320
<212> TYPE: PRT
<213> ORGANISM: Homo sapiens

<400> SEQUENCE: 17

```
Ala Leu Glu His Met Tyr His Asp Leu Gly Leu Val Arg Asp Phe Ser
 1               5                  10                  15

Ile Asn Pro Val Thr Leu Arg Arg Trp Leu Phe Cys Val His Asp Asn
                20                  25                  30

Tyr Arg Asn Asn Pro Phe His Asn Phe Arg His Cys Phe Cys Val Ala
            35                  40                  45

Gln Met Met Tyr Ser Met Val Trp Leu Cys Ser Leu Gln Glu Lys Phe
        50                  55                  60

Ser Gln Thr Asp Ile Leu Ile Leu Met Thr Ala Ala Ile Cys His Asp
 65                  70                  75                  80

Leu Asp His Pro Gly Tyr Asn Asn Thr Tyr Gln Ile Asn Ala Arg Thr
                85                  90                  95

Glu Leu Ala Val Arg Tyr Asn Asp Ile Ser Pro Leu Glu Asn His His
            100                 105                 110

Cys Ala Val Ala Phe Gln Ile Leu Ala Glu Pro Glu Cys Asn Ile Phe
        115                 120                 125

Ser Asn Ile Pro Pro Asp Gly Phe Lys Gln Ile Arg Gln Gly Met Ile
130                 135                 140

Thr Leu Ile Leu Ala Thr Asp Met Ala Arg His Ala Glu Ile Met Asp
145                 150                 155                 160

Ser Phe Lys Glu Lys Met Glu Asn Phe Asp Tyr Ser Asn Glu Glu His
                165                 170                 175

Met Thr Leu Leu Lys Met Ile Leu Ile Lys Cys Cys Asp Ile Ser Asn
            180                 185                 190

Glu Val Arg Pro Met Glu Val Ala Glu Pro Trp Val Asp Cys Leu Leu
        195                 200                 205

Glu Glu Tyr Phe Met Gln Ser Asp Arg Glu Lys Ser Glu Gly Leu Pro
    210                 215                 220

Val Ala Pro Phe Met Asp Arg Asp Lys Val Thr Lys Ala Thr Ala Gln
225                 230                 235                 240

Ile Gly Phe Ile Lys Phe Val Leu Ile Pro Met Phe Glu Thr Val Thr
                245                 250                 255

Lys Leu Phe Pro Met Val Glu Glu Ile Met Leu Gln Pro Leu Trp Glu
            260                 265                 270

Ser Arg Asp Arg Tyr Glu Glu Leu Lys Arg Ile Asp Asp Ala Met Lys
        275                 280                 285

Glu Leu Gln Lys Lys Thr Asp Ser Leu Thr Ser Gly Ala Thr Glu Lys
    290                 295                 300

Ser Arg Glu Arg Ser Arg Asp Val Lys Asn Ser Glu Gly Asp Cys Ala
305                 310                 315                 320
```

-continued

```
<210> SEQ ID NO 18
<211> LENGTH: 1887
<212> TYPE: DNA
<213> ORGANISM: Homo sapiens
<220> FEATURE:
<221> NAME/KEY: CDS
<222> LOCATION: (74)..(1672)

<400> SEQUENCE: 18
ctcccccgcc tcccgcggcg gctggcgtcg ggaaagtaca gtaaaaagtc cgagtgcagc      60
cgccgggcgc agg atg gga tcc ggc tcc tcc agc tac cgg ccc aag gcc      109
            Met Gly Ser Gly Ser Ser Ser Tyr Arg Pro Lys Ala
              1               5                  10 atc tac ctg gac atc gat gga cgc att cag aag gta atc ttc agc aag      157
Ile Tyr Leu Asp Ile Asp Gly Arg Ile Gln Lys Val Ile Phe Ser Lys
         15                  20                  25 tac tgc aac tcc agc gac atc atg gac ctg ttc tgc atc gcc acc ggc      205
Tyr Cys Asn Ser Ser Asp Ile Met Asp Leu Phe Cys Ile Ala Thr Gly
     30                  35                  40 ctg cct cgg aac acg acc atc tcc ctg ctg acc acc gac gac gcc atg      253
Leu Pro Arg Asn Thr Thr Ile Ser Leu Leu Thr Thr Asp Asp Ala Met
 45                  50                  55                  60 gtc tcc atc gac ccc acc atg ccc gcg aat tca gaa cgc act ccg tac      301
Val Ser Ile Asp Pro Thr Met Pro Ala Asn Ser Glu Arg Thr Pro Tyr
                 65                  70                  75 aaa gtg aga cct gtg gcc atc aag caa ctc tcc gag aga gaa gaa tta      349
Lys Val Arg Pro Val Ala Ile Lys Gln Leu Ser Glu Arg Glu Glu Leu
             80                  85                  90 atc cag agc gtg ctg gcg cag gtt gca gag cag ttc tca aga gca ttc      397
Ile Gln Ser Val Leu Ala Gln Val Ala Glu Gln Phe Ser Arg Ala Phe
         95                 100                 105 aaa atc aat gaa ctg aaa gct gaa gtt gca aat cac ttg gct gtc cta      445
Lys Ile Asn Glu Leu Lys Ala Glu Val Ala Asn His Leu Ala Val Leu
     110                 115                 120 gag aaa cgc gtg gaa ttg gaa gga cta aaa gtg gtg gag att gag aaa      493
Glu Lys Arg Val Glu Leu Glu Gly Leu Lys Val Val Glu Ile Glu Lys
125                 130                 135                 140 tgc aag agt gac att aag aag atg agg gag gag ctg gcg gcc aga agc      541
Cys Lys Ser Asp Ile Lys Lys Met Arg Glu Glu Leu Ala Ala Arg Ser
                145                 150                 155 agc agg acc aac tgc ccc tgt aag tac agt ttt ttg gat aac cac aag      589
Ser Arg Thr Asn Cys Pro Cys Lys Tyr Ser Phe Leu Asp Asn His Lys
            160                 165                 170 aag ttg act cct cga cgc gat gtt ccc act tac ccc aag tac ctg ctc      637
Lys Leu Thr Pro Arg Arg Asp Val Pro Thr Tyr Pro Lys Tyr Leu Leu
        175                 180                 185 tct cca gag acc atc gag gcc ctg cgg aag ccg acc ttt gac gtc tgg      685
Ser Pro Glu Thr Ile Glu Ala Leu Arg Lys Pro Thr Phe Asp Val Trp
    190                 195                 200 ctt tgg gag ccc aat gag atg ctg agc tgc ctg gag cac atg tac cac      733
Leu Trp Glu Pro Asn Glu Met Leu Ser Cys Leu Glu His Met Tyr His
205                 210                 215                 220 gac ctc ggg ctg gtc agg gac ttc agc atc aac cct gtc acc ctc agg      781
Asp Leu Gly Leu Val Arg Asp Phe Ser Ile Asn Pro Val Thr Leu Arg
                225                 230                 235 agg tgg ctg ttc tgc gtc cac gac aac tac aga aac aac ccc ttc cac      829
Arg Trp Leu Phe Cys Val His Asp Asn Tyr Arg Asn Asn Pro Phe His
            240                 245                 250 aac ttc cgg cac tgc ttc tgc gtg gcc cag atg atg tac agc atg gtc      877
Asn Phe Arg His Cys Phe Cys Val Ala Gln Met Met Tyr Ser Met Val
        255                 260                 265
```

```
tgg ctc tgc agt ctc cag gag aag ttc tca caa acg gat atc ctg atc    925
Trp Leu Cys Ser Leu Gln Glu Lys Phe Ser Gln Thr Asp Ile Leu Ile
    270                 275                 280 cta atg aca gcg gcc atc tgc cac gat ctg gac cat ccc ggc tac aac    973
Leu Met Thr Ala Ala Ile Cys His Asp Leu Asp His Pro Gly Tyr Asn
285                 290                 295                 300 aac acg tac cag atc aat gcc cgc aca gag ctg gcg gtc cgc tac aat   1021
Asn Thr Tyr Gln Ile Asn Ala Arg Thr Glu Leu Ala Val Arg Tyr Asn
                305                 310                 315 gac atc tca ccg ctg gag aac cac cac tgc gcc gtg gcc ttc cag atc   1069
Asp Ile Ser Pro Leu Glu Asn His His Cys Ala Val Ala Phe Gln Ile
            320                 325                 330 ctc gcc gag cct gag tgc aac atc ttc tcc aac atc cca cct gat ggg   1117
Leu Ala Glu Pro Glu Cys Asn Ile Phe Ser Asn Ile Pro Pro Asp Gly
        335                 340                 345 ttc aag cag atc cga cag gga atg atc aca tta atc ttg gcc act gac   1165
Phe Lys Gln Ile Arg Gln Gly Met Ile Thr Leu Ile Leu Ala Thr Asp
    350                 355                 360 atg gca aga cat gca gaa att atg gat tct ttc aaa gag aaa atg gag   1213
Met Ala Arg His Ala Glu Ile Met Asp Ser Phe Lys Glu Lys Met Glu
365                 370                 375                 380 aat ttt gac tac agc aac gag gag cac atg acc ctg ctg aag atg att   1261
Asn Phe Asp Tyr Ser Asn Glu Glu His Met Thr Leu Leu Lys Met Ile
                385                 390                 395 ttg ata aaa tgc tgt gat atc tct aac gag gtc cgt cca atg gaa gtc   1309
Leu Ile Lys Cys Cys Asp Ile Ser Asn Glu Val Arg Pro Met Glu Val
            400                 405                 410 gca gag cct tgg gtg gac tgt tta tta gag gaa tat ttt atg cag agc   1357
Ala Glu Pro Trp Val Asp Cys Leu Leu Glu Glu Tyr Phe Met Gln Ser
        415                 420                 425 gac cgt gag aag tca gaa ggc ctt cct gtg gca ccg ttc atg gac cga   1405
Asp Arg Glu Lys Ser Glu Gly Leu Pro Val Ala Pro Phe Met Asp Arg
    430                 435                 440 gac aaa gtg acc aag gcc aca gcc cag att ggg ttc atc aag ttt gtc   1453
Asp Lys Val Thr Lys Ala Thr Ala Gln Ile Gly Phe Ile Lys Phe Val
445                 450                 455                 460 ctg atc cca atg ttt gaa aca gtg acc aag ctc ttc ccc atg gtt gag   1501
Leu Ile Pro Met Phe Glu Thr Val Thr Lys Leu Phe Pro Met Val Glu
                465                 470                 475 gag atc atg ctg cag cca ctt tgg gaa tcc cga gat cgc tac gag gag   1549
Glu Ile Met Leu Gln Pro Leu Trp Glu Ser Arg Asp Arg Tyr Glu Glu
            480                 485                 490 ctg aag cgg ata gat gac gcc atg aaa gag tta cag aag aag act gac   1597
Leu Lys Arg Ile Asp Asp Ala Met Lys Glu Leu Gln Lys Lys Thr Asp
        495                 500                 505 agc ttg acg tct ggg gcc acc gag aag tcc aga gag aga agc aga gat   1645
Ser Leu Thr Ser Gly Ala Thr Glu Lys Ser Arg Glu Arg Ser Arg Asp
    510                 515                 520 gtg aaa aac agt gaa gga gac tgt gcc tgaggaaagc gggggcgtg           1692
Val Lys Asn Ser Glu Gly Asp Cys Ala
525                 530 gctgcagttc tggacgggct ggccgagctg cgcgggatcc ttgtgcaggg aagagctgcc  1752
ctgggcacct ggcaccacaa gaccatgttt tctaagaacc attttgttca ctgataaaaa  1812
aaaaaaaaaa ggaattcatg atgctgtaca gaattttatt tttaaactgt ctttaaata   1872 atatattctt atacg                                                   1887
```

```
<210> SEQ ID NO 19
<211> LENGTH: 533
<212> TYPE: PRT
<213> ORGANISM: Homo sapiens

<400> SEQUENCE: 19

Met Gly Ser Gly Ser Ser Tyr Arg Pro Lys Ala Ile Tyr Leu Asp
  1               5                  10                  15

Ile Asp Gly Arg Ile Gln Lys Val Ile Phe Ser Lys Tyr Cys Asn Ser
                 20                  25                  30

Ser Asp Ile Met Asp Leu Phe Cys Ile Ala Thr Gly Leu Pro Arg Asn
             35                  40                  45

Thr Thr Ile Ser Leu Leu Thr Thr Asp Asp Ala Met Val Ser Ile Asp
         50                  55                  60

Pro Thr Met Pro Ala Asn Ser Glu Arg Thr Pro Tyr Lys Val Arg Pro
 65                  70                  75                  80

Val Ala Ile Lys Gln Leu Ser Glu Arg Glu Leu Ile Gln Ser Val
                 85                  90                  95

Leu Ala Gln Val Ala Glu Gln Phe Ser Arg Ala Phe Lys Ile Asn Glu
                100                 105                 110

Leu Lys Ala Glu Val Ala Asn His Leu Ala Val Leu Glu Lys Arg Val
            115                 120                 125

Glu Leu Glu Gly Leu Lys Val Val Glu Ile Glu Lys Cys Lys Ser Asp
        130                 135                 140

Ile Lys Lys Met Arg Glu Glu Leu Ala Ala Arg Ser Ser Arg Thr Asn
145                 150                 155                 160

Cys Pro Cys Lys Tyr Ser Phe Leu Asp Asn His Lys Lys Leu Thr Pro
                165                 170                 175

Arg Arg Asp Val Pro Thr Tyr Pro Lys Tyr Leu Leu Ser Pro Glu Thr
                180                 185                 190

Ile Glu Ala Leu Arg Lys Pro Thr Phe Asp Val Trp Leu Trp Glu Pro
            195                 200                 205

Asn Glu Met Leu Ser Cys Leu Glu His Met Tyr His Asp Leu Gly Leu
        210                 215                 220

Val Arg Asp Phe Ser Ile Asn Pro Val Thr Leu Arg Arg Trp Leu Phe
225                 230                 235                 240

Cys Val His Asp Asn Tyr Arg Asn Asn Pro Phe His Asn Phe Arg His
                245                 250                 255

Cys Phe Cys Val Ala Gln Met Met Tyr Ser Met Val Trp Leu Cys Ser
                260                 265                 270

Leu Gln Glu Lys Phe Ser Gln Thr Asp Ile Leu Ile Leu Met Thr Ala
            275                 280                 285

Ala Ile Cys His Asp Leu Asp His Pro Gly Tyr Asn Asn Thr Tyr Gln
        290                 295                 300

Ile Asn Ala Arg Thr Glu Leu Ala Val Arg Tyr Asn Asp Ile Ser Pro
305                 310                 315                 320

Leu Glu Asn His His Cys Ala Val Ala Phe Gln Ile Leu Ala Glu Pro
                325                 330                 335

Glu Cys Asn Ile Phe Ser Asn Ile Pro Pro Asp Gly Phe Lys Gln Ile
                340                 345                 350

Arg Gln Gly Met Ile Thr Leu Ile Leu Ala Thr Asp Met Ala Arg His
            355                 360                 365

Ala Glu Ile Met Asp Ser Phe Lys Glu Lys Met Glu Asn Phe Asp Tyr
        370                 375                 380
```

```
Ser Asn Glu Glu His Met Thr Leu Leu Lys Met Ile Leu Ile Lys Cys
385                 390                 395                 400

Cys Asp Ile Ser Asn Glu Val Arg Pro Met Glu Val Ala Glu Pro Trp
            405                 410                 415

Val Asp Cys Leu Leu Glu Glu Tyr Phe Met Gln Ser Asp Arg Glu Lys
            420                 425                 430

Ser Glu Gly Leu Pro Val Ala Pro Phe Met Asp Arg Asp Lys Val Thr
        435                 440                 445

Lys Ala Thr Ala Gln Ile Gly Phe Ile Lys Phe Val Leu Ile Pro Met
    450                 455                 460

Phe Glu Thr Val Thr Lys Leu Phe Pro Met Val Glu Glu Ile Met Leu
465                 470                 475                 480

Gln Pro Leu Trp Glu Ser Arg Asp Arg Tyr Glu Glu Leu Lys Arg Ile
                485                 490                 495

Asp Asp Ala Met Lys Glu Leu Gln Lys Lys Thr Asp Ser Leu Thr Ser
            500                 505                 510

Gly Ala Thr Glu Lys Ser Arg Glu Arg Ser Arg Asp Val Lys Asn Ser
        515                 520                 525

Glu Gly Asp Cys Ala
        530

<210> SEQ ID NO 20
<211> LENGTH: 1967
<212> TYPE: DNA
<213> ORGANISM: Homo sapiens
<220> FEATURE:
<221> NAME/KEY: CDS
<222> LOCATION: (2)..(1741)

<400> SEQUENCE: 20
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| c   | tac | ctg | gac | atc | gat | gga | cgc | att | cag | aag | gta | atc | ttc | agc | aag tac | 49 |
|     | Tyr | Leu | Asp | Ile | Asp | Gly | Arg | Ile | Gln | Lys | Val | Ile | Phe | Ser | Lys Tyr |  |
|     | 1   |     |     |     | 5   |     |     |     |     | 10  |     |     |     |     | 15      |  |

```
tgc aac tcc agc gac atc atg gac ctg ttc tgc atc gcc acc ggc ctg        97
Cys Asn Ser Ser Asp Ile Met Asp Leu Phe Cys Ile Ala Thr Gly Leu
            20                  25                  30 cct cgg aac acg acc atc tcc ctg ctg acc acc gac gac gcc atg gtc       145
Pro Arg Asn Thr Thr Ile Ser Leu Leu Thr Thr Asp Asp Ala Met Val
        35                  40                  45 tcc atc gac ccc acc atg ccc gcg aat tca gaa cgc act ccg tac aaa       193
Ser Ile Asp Pro Thr Met Pro Ala Asn Ser Glu Arg Thr Pro Tyr Lys
    50                  55                  60 gtg aga cct gtg gcc atc aag caa ctc tcc gct gat gtc gag gac aag       241
Val Arg Pro Val Ala Ile Lys Gln Leu Ser Ala Asp Val Glu Asp Lys
65                  70                  75                  80 aga acc aca agc cgt ggc cag tct gct gag aga cca ctg agg gac aga       289
Arg Thr Thr Ser Arg Gly Gln Ser Ala Glu Arg Pro Leu Arg Asp Arg
                85                  90                  95 cgg gtt gtg ggc ctg gag cag ccc cgg agg gaa gga gca ttt gaa agt       337
Arg Val Val Gly Leu Glu Gln Pro Arg Arg Glu Gly Ala Phe Glu Ser
            100                 105                 110 gga cag gta gag ccc agg ccc aga gag ccc cag ggc tgc tac cag gaa       385
Gly Gln Val Glu Pro Arg Pro Arg Glu Pro Gln Gly Cys Tyr Gln Glu
        115                 120                 125 ggc cag cgc atc cct cca gag aga gaa gaa tta atc cag agc gtg ctg       433
Gly Gln Arg Ile Pro Pro Glu Arg Glu Glu Leu Ile Gln Ser Val Leu
    130                 135                 140
```

```
gcg cag gtt gca gag cag ttc tca aga gca ttc aaa atc aat gaa ctg      481
Ala Gln Val Ala Glu Gln Phe Ser Arg Ala Phe Lys Ile Asn Glu Leu
145                 150                 155                 160 aaa gct gaa gtt gca aat cac ttg gct gtc cta gag aaa cgc gtg gaa      529
Lys Ala Glu Val Ala Asn His Leu Ala Val Leu Glu Lys Arg Val Glu
                165                 170                 175 ttg gaa gga cta aaa gtg gtg gag att gag aaa tgc aag agt gac att      577
Leu Glu Gly Leu Lys Val Val Glu Ile Glu Lys Cys Lys Ser Asp Ile
        180                 185                 190 aag aag atg agg gag gag ctg gcg gcc aga agc agc agg acc aac tgc      625
Lys Lys Met Arg Glu Glu Leu Ala Ala Arg Ser Ser Arg Thr Asn Cys
    195                 200                 205 ccc tgt aag tac agt ttt ttg gat aac cac aag aag ttg act cct cga      673
Pro Cys Lys Tyr Ser Phe Leu Asp Asn His Lys Lys Leu Thr Pro Arg
210                 215                 220 cgc gat gtt ccc act tac ccc aag tac ctg ctc tct cca gag acc atc      721
Arg Asp Val Pro Thr Tyr Pro Lys Tyr Leu Leu Ser Pro Glu Thr Ile
225                 230                 235                 240 gag gcc ctg cgg aag ccg acc ttt gac gtc tgg ctt tgg gag ccc aat      769
Glu Ala Leu Arg Lys Pro Thr Phe Asp Val Trp Leu Trp Glu Pro Asn
                245                 250                 255 gag atg ctg agc tgc ctg gag cac atg tac cac gac ctc ggg ctg gtc      817
Glu Met Leu Ser Cys Leu Glu His Met Tyr His Asp Leu Gly Leu Val
            260                 265                 270 agg gac ttc agc atc aac cct gtc acc ctc agg agg tgg ctg ttc tgc      865
Arg Asp Phe Ser Ile Asn Pro Val Thr Leu Arg Arg Trp Leu Phe Cys
        275                 280                 285 gtc cac gac aac tac aga aac aac ccc ttc cac aac ttc cgg cac tgc      913
Val His Asp Asn Tyr Arg Asn Asn Pro Phe His Asn Phe Arg His Cys
    290                 295                 300 ttc tgc gtg gcc cag atg atg tac agc atg gtc tgg ctc tgc agt ctc      961
Phe Cys Val Ala Gln Met Met Tyr Ser Met Val Trp Leu Cys Ser Leu
305                 310                 315                 320 cag gag aag ttc tca caa acg gat atc ctg atc cta atg aca gcg gcc     1009
Gln Glu Lys Phe Ser Gln Thr Asp Ile Leu Ile Leu Met Thr Ala Ala
                325                 330                 335 atc tgc cac gat ctg gac cat ccc ggc tac aac aac acg tac cag atc     1057
Ile Cys His Asp Leu Asp His Pro Gly Tyr Asn Asn Thr Tyr Gln Ile
            340                 345                 350 aat gcc cgc aca gag ctg gcg gtc cgc tac aat gac atc tca ccg ctg     1105
Asn Ala Arg Thr Glu Leu Ala Val Arg Tyr Asn Asp Ile Ser Pro Leu
        355                 360                 365 gag aac cac cac tgc gcc gtg gcc ttc cag atc ctc gcc gag cct gag     1153
Glu Asn His His Cys Ala Val Ala Phe Gln Ile Leu Ala Glu Pro Glu
    370                 375                 380 tgc aac atc ttc tcc aac atc cca cct gat ggg ttc aag cag atc cga     1201
Cys Asn Ile Phe Ser Asn Ile Pro Pro Asp Gly Phe Lys Gln Ile Arg
385                 390                 395                 400 cag gga atg atc aca tta atc ttg gcc act gac atg gca aga cat gca     1249
Gln Gly Met Ile Thr Leu Ile Leu Ala Thr Asp Met Ala Arg His Ala
                405                 410                 415 gaa att atg gat tct ttc aaa gag aaa atg gag aat ttt gac tac agc     1297
Glu Ile Met Asp Ser Phe Lys Glu Lys Met Glu Asn Phe Asp Tyr Ser
            420                 425                 430 aac gag gag cac atg acc ctg ctg aag atg att ttg ata aaa tgc tgt     1345
Asn Glu Glu His Met Thr Leu Leu Lys Met Ile Leu Ile Lys Cys Cys
        435                 440                 445 gat atc tct aac gag gtc cgt cca atg gaa gtc gca gag cct tgg gtg     1393
Asp Ile Ser Asn Glu Val Arg Pro Met Glu Val Ala Glu Pro Trp Val
    450                 455                 460
```

```
gac tgt tta tta gag gaa tat ttt atg cag agc gac cgt gag aag tca    1441
Asp Cys Leu Leu Glu Glu Tyr Phe Met Gln Ser Asp Arg Glu Lys Ser
465                 470                 475                 480 gaa ggc ctt cct gtg gca ccg ttc atg gac cga gac aaa gtg acc aag    1489
Glu Gly Leu Pro Val Ala Pro Phe Met Asp Arg Asp Lys Val Thr Lys
                485                 490                 495 gcc aca gcc cag att ggg ttc atc aag ttt gtc ctg atc cca atg ttt    1537
Ala Thr Ala Gln Ile Gly Phe Ile Lys Phe Val Leu Ile Pro Met Phe
            500                 505                 510 gaa aca gtg acc aag ctc ttc ccc atg gtt gag gag atc atg ctg cag    1585
Glu Thr Val Thr Lys Leu Phe Pro Met Val Glu Glu Ile Met Leu Gln
        515                 520                 525 cca ctt tgg gaa tcc cga gat cgc tac gag gag ctg aag cgg ata gat    1633
Pro Leu Trp Glu Ser Arg Asp Arg Tyr Glu Glu Leu Lys Arg Ile Asp
    530                 535                 540 gac gcc atg aaa gag tta cag aag aag act gac agc ttg acg tct ggg    1681
Asp Ala Met Lys Glu Leu Gln Lys Lys Thr Asp Ser Leu Thr Ser Gly
545                 550                 555                 560 gcc acc gag aag tcc aga gag aga agc aga gat gtg aaa aac agt gaa    1729
Ala Thr Glu Lys Ser Arg Glu Arg Ser Arg Asp Val Lys Asn Ser Glu
                565                 570                 575 gga gac tgt gcc tgaggaaagc gggggcgtg gctgcagttc tggacgggct         1781
Gly Asp Cys Ala
            580 ggccgagctg cgcgggatcc ttgtgcaggg aagagctgcc ctgggcacct ggcaccacaa  1841 gaccatgttt tctaagaacc attttgttca ctgatacaaa aaaaaaaaa ggaattcatg   1901 atgctgtaca gaattttatt tttaaactgt cttttaaata atatattctt atacggaaaa  1961 aaaaaa                                                             1967

<210> SEQ ID NO 21
<211> LENGTH: 580
<212> TYPE: PRT
<213> ORGANISM: Homo sapiens

<400> SEQUENCE: 21

Tyr Leu Asp Ile Asp Gly Arg Ile Gln Lys Val Ile Phe Ser Lys Tyr
1               5                   10                  15

Cys Asn Ser Ser Asp Ile Met Asp Leu Phe Cys Ile Ala Thr Gly Leu
                20                  25                  30

Pro Arg Asn Thr Thr Ile Ser Leu Leu Thr Thr Asp Asp Ala Met Val
            35                  40                  45

Ser Ile Asp Pro Thr Met Pro Ala Asn Ser Glu Arg Thr Pro Tyr Lys
        50                  55                  60

Val Arg Pro Val Ala Ile Lys Gln Leu Ser Ala Asp Val Glu Asp Lys
65                  70                  75                  80

Arg Thr Thr Ser Arg Gly Gln Ser Ala Glu Arg Pro Leu Arg Asp Arg
                85                  90                  95

Arg Val Val Gly Leu Glu Gln Pro Arg Arg Glu Gly Ala Phe Glu Ser
            100                 105                 110

Gly Gln Val Glu Pro Arg Pro Glu Pro Gln Gly Cys Tyr Gln Glu
        115                 120                 125

Gly Gln Arg Ile Pro Pro Glu Arg Glu Glu Leu Ile Gln Ser Val Leu
    130                 135                 140

Ala Gln Val Ala Glu Gln Phe Ser Arg Ala Phe Lys Ile Asn Glu Leu
145                 150                 155                 160
```

```
Lys Ala Glu Val Ala Asn His Leu Ala Val Leu Glu Lys Arg Val Glu
                165                 170                 175

Leu Glu Gly Leu Lys Val Val Glu Ile Glu Lys Cys Lys Ser Asp Ile
            180                 185                 190

Lys Lys Met Arg Glu Glu Leu Ala Ala Arg Ser Ser Arg Thr Asn Cys
        195                 200                 205

Pro Cys Lys Tyr Ser Phe Leu Asp Asn His Lys Lys Leu Thr Pro Arg
    210                 215                 220

Arg Asp Val Pro Thr Tyr Pro Lys Tyr Leu Leu Ser Pro Glu Thr Ile
225                 230                 235                 240

Glu Ala Leu Arg Lys Pro Thr Phe Asp Val Trp Leu Trp Glu Pro Asn
            245                 250                 255

Glu Met Leu Ser Cys Leu Glu His Met Tyr His Asp Leu Gly Leu Val
            260                 265                 270

Arg Asp Phe Ser Ile Asn Pro Val Thr Leu Arg Arg Trp Leu Phe Cys
        275                 280                 285

Val His Asp Asn Tyr Arg Asn Asn Pro Phe His Asn Phe Arg His Cys
    290                 295                 300

Phe Cys Val Ala Gln Met Met Tyr Ser Met Val Trp Leu Cys Ser Leu
305                 310                 315                 320

Gln Glu Lys Phe Ser Gln Thr Asp Ile Leu Ile Leu Met Thr Ala Ala
            325                 330                 335

Ile Cys His Asp Leu Asp His Pro Gly Tyr Asn Asn Thr Tyr Gln Ile
            340                 345                 350

Asn Ala Arg Thr Glu Leu Ala Val Arg Tyr Asn Asp Ile Ser Pro Leu
        355                 360                 365

Glu Asn His His Cys Ala Val Ala Phe Gln Ile Leu Ala Glu Pro Glu
    370                 375                 380

Cys Asn Ile Phe Ser Asn Ile Pro Pro Asp Gly Phe Lys Gln Ile Arg
385                 390                 395                 400

Gln Gly Met Ile Thr Leu Ile Leu Ala Thr Asp Met Ala Arg His Ala
            405                 410                 415

Glu Ile Met Asp Ser Phe Lys Glu Lys Met Glu Asn Phe Asp Tyr Ser
            420                 425                 430

Asn Glu Glu His Met Thr Leu Leu Lys Met Ile Leu Ile Lys Cys Cys
        435                 440                 445

Asp Ile Ser Asn Glu Val Arg Pro Met Glu Val Ala Glu Pro Trp Val
    450                 455                 460

Asp Cys Leu Leu Glu Glu Tyr Phe Met Gln Ser Asp Arg Glu Lys Ser
465                 470                 475                 480

Glu Gly Leu Pro Val Ala Pro Phe Met Asp Arg Asp Lys Val Thr Lys
            485                 490                 495

Ala Thr Ala Gln Ile Gly Phe Ile Lys Phe Val Leu Ile Pro Met Phe
            500                 505                 510

Glu Thr Val Thr Lys Leu Phe Pro Met Val Glu Glu Ile Met Leu Gln
        515                 520                 525

Pro Leu Trp Glu Ser Arg Asp Arg Tyr Glu Glu Leu Lys Arg Ile Asp
    530                 535                 540

Asp Ala Met Lys Glu Leu Gln Lys Lys Thr Asp Ser Leu Thr Ser Gly
545                 550                 555                 560
```

-continued

```
Ala Thr Glu Lys Ser Arg Glu Arg Ser Arg Asp Val Lys Asn Ser Glu
            565                 570                 575

Gly Asp Cys Ala
        580

<210> SEQ ID NO 22
<211> LENGTH: 1457
<212> TYPE: DNA
<213> ORGANISM: Homo sapiens
<220> FEATURE:
<221> NAME/KEY: CDS
<222> LOCATION: (164)..(1453)

<400> SEQUENCE: 22
ggctcccggg cgtcccgggc cggtggcgg cgcggctgtg gttggctgag cgccgcgggc         60 cgcccccgc  cgcccctc   cctgctccc  ctccccgcc  tcccgcggcg  gctggcgtcg      120
ggaaagtaca gtaaaaagtc cgagtgcagc cgccgggcgc agg atg gga tcc ggc         175
                                              Met Gly Ser Gly
                                                1 tcc tcc agc tac cgg ccc aag gcc atc tac ctg gac atc gat gga cgc         223
Ser Ser Ser Tyr Arg Pro Lys Ala Ile Tyr Leu Asp Ile Asp Gly Arg
  5                  10                 15                  20 att cag aag gta atc ttc agc aag tac tgc aac tcc agc gac atc atg         271
Ile Gln Lys Val Ile Phe Ser Lys Tyr Cys Asn Ser Ser Asp Ile Met
             25                  30                  35 gac ctg ttc tgc atc gcc acc ggc ctg cct cgg aac acg acc atc tcc         319
Asp Leu Phe Cys Ile Ala Thr Gly Leu Pro Arg Asn Thr Thr Ile Ser
         40                  45                  50 ctg ctg acc acc gac gac gcc atg gtc tcc atc gac ccc acc atg ccc         367
Leu Leu Thr Thr Asp Asp Ala Met Val Ser Ile Asp Pro Thr Met Pro
     55                  60                  65 gcg aat tca gaa cgc act ccg tac aaa gtg aga cct gtg gcc atc aag         415
Ala Asn Ser Glu Arg Thr Pro Tyr Lys Val Arg Pro Val Ala Ile Lys
 70                  75                  80 caa ctc tcc gag aga gaa gaa tta atc cag agc gtg ctg gcg cag gtt         463
Gln Leu Ser Glu Arg Glu Glu Leu Ile Gln Ser Val Leu Ala Gln Val
 85                  90                  95                 100 gca gag cag ttc tca aga gca ttc aaa atc aat gaa ctg aaa gct gaa         511
Ala Glu Gln Phe Ser Arg Ala Phe Lys Ile Asn Glu Leu Lys Ala Glu
                105                 110                 115 gtt gca aat cac ttg gct gtc cta gag aaa cgc gtg gaa ttg gaa gga         559
Val Ala Asn His Leu Ala Val Leu Glu Lys Arg Val Glu Leu Glu Gly
            120                 125                 130 cta aaa gtg gtg gag att gag aaa tgc aag agt gac att aag aag atg         607
Leu Lys Val Val Glu Ile Glu Lys Cys Lys Ser Asp Ile Lys Lys Met
        135                 140                 145 agg gag gag ctg gcg gcc aga agc agc agg acc aac tgc ccc tgt aag         655
Arg Glu Glu Leu Ala Ala Arg Ser Ser Arg Thr Asn Cys Pro Cys Lys
    150                 155                 160 tac agt ttt ttg gat aac cac aag aag ttg act cct cga cgc gat gtt         703
Tyr Ser Phe Leu Asp Asn His Lys Lys Leu Thr Pro Arg Arg Asp Val
165                 170                 175                 180 ccc act tac ccc aag tac ctg ctc tct cca gag acc atc gag gcc ctg         751
Pro Thr Tyr Pro Lys Tyr Leu Leu Ser Pro Glu Thr Ile Glu Ala Leu
                185                 190                 195 cgg aag ccg acc ttt gac gtc tgg ctt tgg gag ccc aat gag atg ctg         799
Arg Lys Pro Thr Phe Asp Val Trp Leu Trp Glu Pro Asn Glu Met Leu
            200                 205                 210
```

-continued

```
agc tgc ctg gag cac atg tac cac gac ctc ggg ctg gtc agg gac ttc      847
Ser Cys Leu Glu His Met Tyr His Asp Leu Gly Leu Val Arg Asp Phe
    215                 220                 225 agc atc aac cct gtc acc ctc agg agg tgg ctg ttc tgc gtc cac gac      895
Ser Ile Asn Pro Val Thr Leu Arg Arg Trp Leu Phe Cys Val His Asp
230                 235                 240 aac tac aga aac aac ccc ttc cac aac ttc cgg cac tgc ttc tgc gtg      943
Asn Tyr Arg Asn Asn Pro Phe His Asn Phe Arg His Cys Phe Cys Val
245                 250                 255                 260 gcc cag atg atg tac agc atg gtc tgg ctc tgc agt ctc cag gag aag      991
Ala Gln Met Met Tyr Ser Met Val Trp Leu Cys Ser Leu Gln Glu Lys
                265                 270                 275 ttc tca caa acg gat atc ctg atc cta atg aca gcg gcc atc tgc cac     1039
Phe Ser Gln Thr Asp Ile Leu Ile Leu Met Thr Ala Ala Ile Cys His
        280                 285                 290 gat ctg gac cat ccc ggc tac aac aac acg tac cag atc aat gcc cgc     1087
Asp Leu Asp His Pro Gly Tyr Asn Asn Thr Tyr Gln Ile Asn Ala Arg
            295                 300                 305 aca gag ctg gcg gtc cgc tac aat gac atc tca ccg ctg gag aac cac     1135
Thr Glu Leu Ala Val Arg Tyr Asn Asp Ile Ser Pro Leu Glu Asn His
                310                 315                 320 cac tgc gcc gtg gcc ttc cag atc ctc gcc gag cct gag tgc aac atc     1183
His Cys Ala Val Ala Phe Gln Ile Leu Ala Glu Pro Glu Cys Asn Ile
325                 330                 335                 340 ttc tcc aac atc cca cct gat ggg ttc aag cag atc cga cag gga atg     1231
Phe Ser Asn Ile Pro Pro Asp Gly Phe Lys Gln Ile Arg Gln Gly Met
                345                 350                 355 atc aca tta atc ttg gcc act gac atg gca aga cat gca gaa att atg     1279
Ile Thr Leu Ile Leu Ala Thr Asp Met Ala Arg His Ala Glu Ile Met
        360                 365                 370 gat tct ttc aaa gag aaa atg gag aat ttt gac tac agc aac gag gag     1327
Asp Ser Phe Lys Glu Lys Met Glu Asn Phe Asp Tyr Ser Asn Glu Glu
            375                 380                 385 cac atg acc ctg ctg aag atg att ttg ata aaa tgc tgt gat atc tct     1375
His Met Thr Leu Leu Lys Met Ile Leu Ile Lys Cys Cys Asp Ile Ser
                390                 395                 400 aac gag gtc cgt cca atg gaa gtc gca gag cct tgg gtg gac tgt tta     1423
Asn Glu Val Arg Pro Met Glu Val Ala Glu Pro Trp Val Asp Cys Leu
405                 410                 415                 420 tta gag gaa tat ttt atg cag agc gac cgt gaga                        1457
Leu Glu Glu Tyr Phe Met Gln Ser Asp Arg
                425                 430
```

<210> SEQ ID NO 23
<211> LENGTH: 430
<212> TYPE: PRT
<213> ORGANISM: Homo sapiens

<400> SEQUENCE: 23

```
Met Gly Ser Gly Ser Ser Tyr Arg Pro Lys Ala Ile Tyr Leu Asp
 1               5                  10                  15

Ile Asp Gly Arg Ile Gln Lys Val Ile Phe Ser Lys Tyr Cys Asn Ser
            20                  25                  30

Ser Asp Ile Met Asp Leu Phe Cys Ile Ala Thr Gly Leu Pro Arg Asn
        35                  40                  45

Thr Thr Ile Ser Leu Leu Thr Thr Asp Asp Ala Met Val Ser Ile Asp
    50                  55                  60

Pro Thr Met Pro Ala Asn Ser Glu Arg Thr Pro Tyr Lys Val Arg Pro
65                  70                  75                  80
```

-continued

```
Val Ala Ile Lys Gln Leu Ser Glu Arg Glu Glu Leu Ile Gln Ser Val
                85                  90                  95

Leu Ala Gln Val Ala Glu Gln Phe Ser Arg Ala Phe Lys Ile Asn Glu
            100                 105                 110

Leu Lys Ala Glu Val Ala Asn His Leu Ala Val Leu Glu Lys Arg Val
        115                 120                 125

Glu Leu Glu Gly Leu Lys Val Val Glu Ile Glu Lys Cys Lys Ser Asp
    130                 135                 140

Ile Lys Lys Met Arg Glu Glu Leu Ala Ala Arg Ser Ser Arg Thr Asn
145                 150                 155                 160

Cys Pro Cys Lys Tyr Ser Phe Leu Asp Asn His Lys Lys Leu Thr Pro
                165                 170                 175

Arg Arg Asp Val Pro Thr Tyr Pro Lys Tyr Leu Leu Ser Pro Glu Thr
            180                 185                 190

Ile Glu Ala Leu Arg Lys Pro Thr Phe Asp Val Trp Leu Trp Glu Pro
        195                 200                 205

Asn Glu Met Leu Ser Cys Leu Glu His Met Tyr His Asp Leu Gly Leu
    210                 215                 220

Val Arg Asp Phe Ser Ile Asn Pro Val Thr Leu Arg Arg Trp Leu Phe
225                 230                 235                 240

Cys Val His Asp Asn Tyr Arg Asn Asn Pro Phe His Asn Phe Arg His
                245                 250                 255

Cys Phe Cys Val Ala Gln Met Met Tyr Ser Met Val Trp Leu Cys Ser
            260                 265                 270

Leu Gln Glu Lys Phe Ser Gln Thr Asp Ile Leu Ile Leu Met Thr Ala
        275                 280                 285

Ala Ile Cys His Asp Leu Asp His Pro Gly Tyr Asn Asn Thr Tyr Gln
    290                 295                 300

Ile Asn Ala Arg Thr Glu Leu Ala Val Arg Tyr Asn Asp Ile Ser Pro
305                 310                 315                 320

Leu Glu Asn His His Cys Ala Val Ala Phe Gln Ile Leu Ala Glu Pro
                325                 330                 335

Glu Cys Asn Ile Phe Ser Asn Ile Pro Pro Asp Gly Phe Lys Gln Ile
            340                 345                 350

Arg Gln Gly Met Ile Thr Leu Ile Leu Ala Thr Asp Met Ala Arg His
        355                 360                 365

Ala Glu Ile Met Asp Ser Phe Lys Glu Lys Met Glu Asn Phe Asp Tyr
    370                 375                 380

Ser Asn Glu Glu His Met Thr Leu Leu Lys Met Ile Leu Ile Lys Cys
385                 390                 395                 400

Cys Asp Ile Ser Asn Glu Val Arg Pro Met Glu Val Ala Glu Pro Trp
                405                 410                 415

Val Asp Cys Leu Leu Glu Glu Tyr Phe Met Gln Ser Asp Arg
            420                 425                 430

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: FLAG
      epitope

<400> SEQUENCE: 24

Asp Thr Lys Asp Asp Asp Asp Lys
 1               5
```

```
<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 25
tagaccatgg actacaagga cgacgatgac aagatggacg cattcagaag cact         54

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 26
cgaggagtca acttcttg                                                  18
```